(12) United States Patent
Brondum et al.

(10) Patent No.: US 12,163,944 B2
(45) Date of Patent: *Dec. 10, 2024

(54) MULTI-FUNCTIONAL WATER QUALITY SENSOR

(71) Applicant: Masco Corporation, Livonia, MI (US)

(72) Inventors: Klaus Brondum, Ann Arbor, MI (US); Michael McCague, Escondido, CA (US); Mark A. Burns, Ann Arbor, MI (US); Wen-Chi Lin, Saline, MI (US)

(73) Assignees: The Regents of the University of Michigan, Ann Arbor, MI (US); Masco Corporation, Livonia, MI (US)

( * ) Notice: Subject to any disclaimer, the term of this patent is extended or adjusted under 35 U.S.C. 154(b) by 880 days.

This patent is subject to a terminal disclaimer.

(21) Appl. No.: 15/655,536

(22) Filed: Jul. 20, 2017

(65) Prior Publication Data

US 2019/0025273 A1  Jan. 24, 2019

(51) Int. Cl.
*G01N 33/18* (2006.01)
*C02F 1/00* (2023.01)
(Continued)

(52) U.S. Cl.
CPC .............. *G01N 33/18* (2013.01); *C02F 1/008* (2013.01); *C02F 1/76* (2013.01); *G01N 27/07* (2013.01); *G01N 27/4165* (2013.01); *G01N 27/4166* (2013.01); *C02F 2103/42* (2013.01); *C02F 2209/04* (2013.01); *C02F 2209/05* (2013.01); *C02F 2209/06* (2013.01); *C02F 2209/07* (2013.01)

(58) Field of Classification Search
CPC .............. C02F 2103/42; C02F 2209/04; C02F 2209/05; C02F 2209/06; C02F 2209/07; C02F 1/008; G01N 27/07; G01N 27/4165; G01N 27/4166; G01N 33/18
See application file for complete search history.

(56) References Cited

U.S. PATENT DOCUMENTS 6,255,117 B1   7/2001   Johnson
6,894,270 B2   5/2005   Bailey
(Continued)

FOREIGN PATENT DOCUMENTS

CN   205910610 U   1/2017

OTHER PUBLICATIONS

Jang, et al.; "State-of-the-art Lab Chip Sensors for Environmental Water Monitoring"; Measurment Science and Technology; 2011; 18 pages; vol. 22.
(Continued)

*Primary Examiner* — Patrick Orme
(74) *Attorney, Agent, or Firm* — Reising Ethington P.C.

(57) ABSTRACT

A multi-functional sensor assembly includes an electrically non-conductive substrate defining at least a distal region, intermediary region, and proximal region that are each covered with electrically conductive traces. The proximal region is configured to be exposed to a media to be sensed and the distal and intermediary regions are configured to be protected from the media. The electrically conductive traces are connected to one or more electrodes to sense one or more of alkalinity, cyanuric acid concentration, or oxidant concentration of the media.

22 Claims, 15 Drawing Sheets

(51) Int. Cl.
*C02F 1/76* (2023.01)
*C02F 103/42* (2006.01)
*G01N 27/07* (2006.01)
*G01N 27/416* (2006.01)

(56) References Cited

U.S. PATENT DOCUMENTS

| | | | |
|---|---|---|---|
| 7,189,314 B1* | 3/2007 | Pace | G01N 33/1886 |
| | | | 204/412 |
| 7,516,939 B2 | 4/2009 | Bailey | |
| 7,581,437 B2 | 9/2009 | Colby et al. | |
| 8,987,000 B2 | 3/2015 | Evtodienko et al. | |
| 8,993,337 B2 | 3/2015 | Evtodienko et al. | |
| 2003/0147777 A1 | 8/2003 | Ghanekar | |
| 2003/0198428 A1* | 10/2003 | Humpston | B23K 35/26 |
| | | | 385/16 |
| 2004/0104130 A1 | 6/2004 | Mosley et al. | |
| 2005/0252790 A1 | 11/2005 | Dobson et al. | |
| 2007/0125663 A1 | 6/2007 | Sasanuma et al. | |
| 2008/0148842 A1* | 6/2008 | Oda | G01F 1/6845 |
| | | | 73/204.26 |
| 2008/0258742 A1 | 10/2008 | Dimitrakopoulos et al. | |
| 2008/0295897 A1 | 12/2008 | Vincent | |
| 2009/0282627 A1* | 11/2009 | Porat | E04H 4/1281 |
| | | | 15/1.7 |
| 2011/0107832 A1 | 5/2011 | Sakuma | |
| 2012/0216605 A1* | 8/2012 | Silveri | G01N 27/08 |
| | | | 73/61.41 |
| 2013/0145840 A1 | 6/2013 | Asano et al. | |
| 2014/0083865 A1 | 3/2014 | Rowhani et al. | |
| 2014/0212336 A1 | 7/2014 | Kido et al. | |
| 2014/0295569 A1 | 10/2014 | Evtodienko et al. | |
| 2014/0299471 A1 | 10/2014 | Mosley et al. | |
| 2015/0177042 A1 | 6/2015 | Song et al. | |
| 2016/0054249 A1 | 2/2016 | Rateick | |
| 2016/0209346 A1 | 7/2016 | Brondum et al. | |
| 2016/0232421 A1 | 8/2016 | Decker et al. | |
| 2016/0299096 A1 | 10/2016 | Greenwood et al. | |

OTHER PUBLICATIONS

Lin, et al.; Mulitfunctional Water Sensors for pH, ORP, and Conductivity Using Only Microfabricated Platinum Electrodes; Sensors; 2017; 9 pages; vol. 17, 1655.
Pellegrino, et al.; Robust Multi-Parameter Sensing Probe for Water Monitoring Based on ALD-Coated Metallic Micro-patterns and Carbon Nanotube Printing; IEEE NEMS; 2016; 3 pages.
European Search Report; Application No. 18182253; Mailing Date Dec. 11, 2018; 9 Pages.
Australian Examination Report corresponding to application 2018204817, dated May 3, 2023, 4 pages.
European Office Action corresponding to application 18182253.7, dated May 8, 2020, 7 pages.
European Office Action corresponding to application 18182253.7, dated May 23, 2022, 5 pages.
European Summons to attend Oral Proceedings corresponding to application 18182253.7, dated Apr. 16, 2024, 10 pages.

* cited by examiner

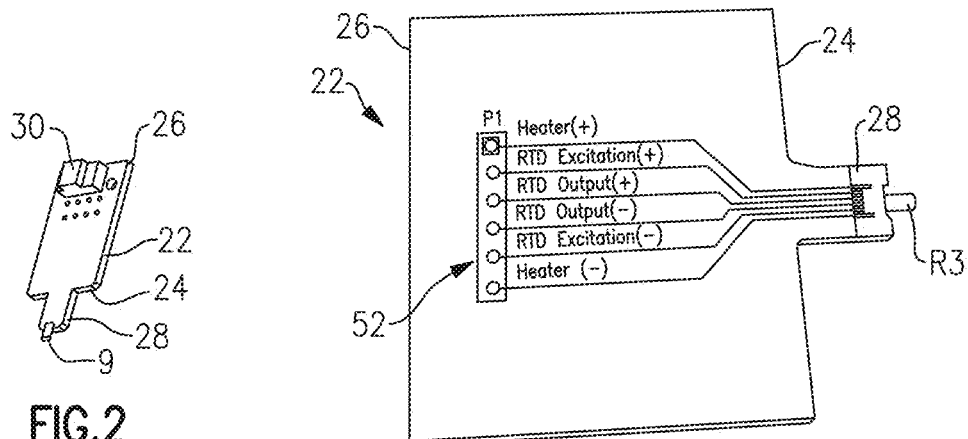
FIG.2
FIG.3
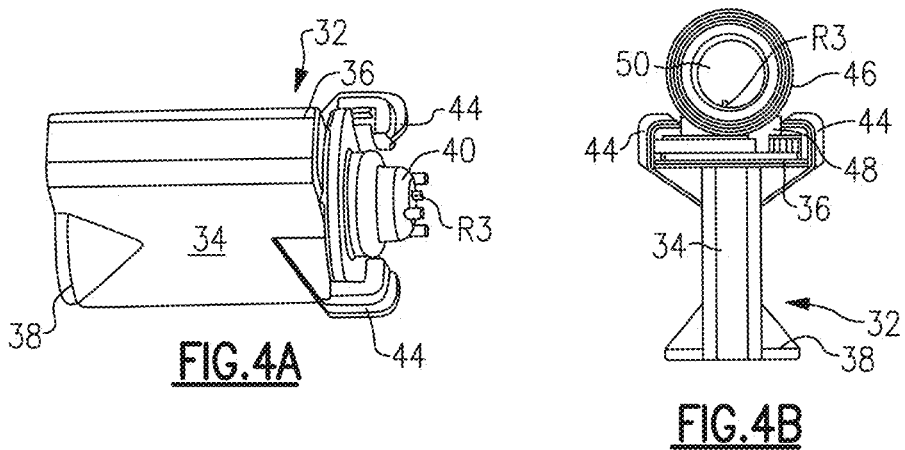
FIG.4A
FIG.4B
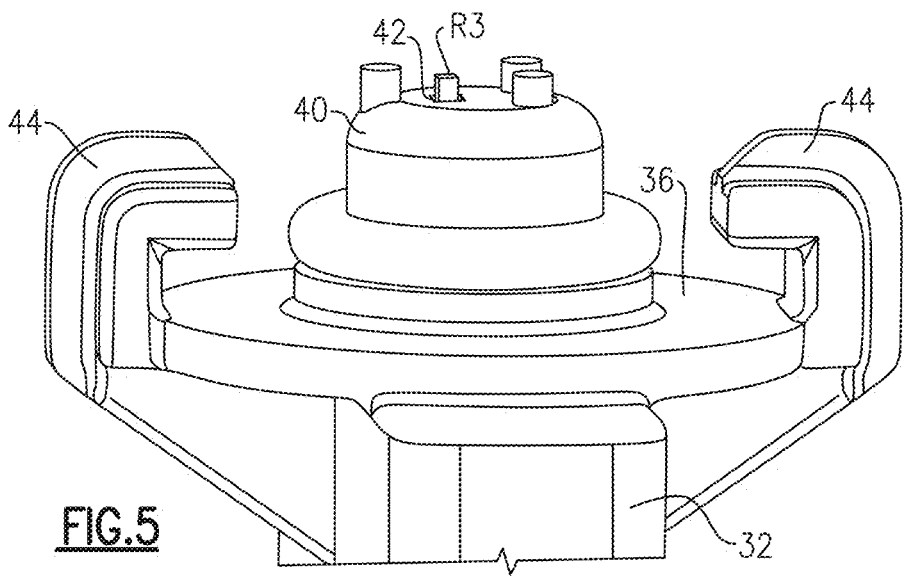
FIG.5

MULTI-FUNCTIONAL WATER QUALITY SENSOR

CROSS REFERENCE TO RELATED APPLICATION

This application relates to U.S. Non Provisional patent application Ser. No. 14/934,499, which is assigned to the assignees hereof and incorporated herein by reference in its entirety.

COMMON OWNERSHIP

This application and U.S. Nonprovisional patent application Ser. No. 14/934,499 were, as of the effective filing date(s) of the invention(s) claimed herein, owned by, or subject to obligations of assignment to, Masco Corporation (17450 Masco Way, Livonia Michigan, 48152) and the Regents of the University of Michigan (1600 Huron Parkway, $2^{nd}$ Floor, Ann Arbor Michigan, 48109).

BACKGROUND

The present disclosure generally relates to a multi-functional flow sensor. One example of a commercial application for this type of sensor is a spa. Typical sensors for monitoring water quality in a spa include in-line sensors, which monitor physical parameters, temperature and flow, and chemical sensors, which monitor conductivity, Oxidation Reduction Potential (ORP) and acidity (pH). These sensors provide information that is used to maintain healthy and safe spa water.

Temperature sensors traditionally used within the industry are of Resistive Temperature Detector (RTD) type, and are typically configured with a stainless steel dome to prevent malfunction due to corrosion and water ingress issues. The protective dome represents a considerable thermal mass that translates into slow response time of the sensor. The temperature sensor has several uses in spa operation, e.g. to determine the temperature of the spa for safety and comfort purposes, to determine temperature correction basis for conductivity measurement, and to provide overheat protection of a water heater for safety purposes.

Flow sensors for water use are based on a diverse range of concepts including anemometer and impeller types, for example. The impeller type is vulnerable to debris and corrosion, which can block spin wheel rotation and create false low readings. The anemometer type relies on a measurement of difference in resistance of two wires immersed in water, with one the wires being heated. Drift can be caused by precipitation on the heated wire and general elevated corrosion of metal wire. In addition, the anemometer is prone to malfunction when operated out of water or in "no flow" conditions. In some configurations, the anemometer will also have high power consumption preventing standalone battery operation. While flow sensors can sometimes be preferred, both flow and pressure sensors are used in spa operation, as measure of filter conditions, i.e. measure of degree of blockage, and as protection of the water heater against overheat conditions.

Conductivity sensors adopted by industry can be as simple as documenting the DC resistance of two water immersed wires operated at an AC frequency. Sometimes conductivity is translated into total dissolved solids (TDS), requiring a temperature correction of conductivity to produce reliable results. The need for conductivity measure is based on the observation that corrosion generally increases with increased conductivity and therefore translates into general corrosion performance of metal components in spa environments. Further, conductivity gives a general understanding of the amount of chemicals that have been added over time, and which have accumulated in the spa. Finally, conductivity serves as a basis for optimal operation of chlorine generator by electrolysis.

Traditional ORP and pH sensors are based on reference electrodes, such as silver chloride electrodes, which produce a fixed potential against which other measures can be referenced. A common silver reference electrode is an example of an equilibrium reference. Specific problems are recognized in the operation of pH and ORP sensors based on equilibrium references. First, a membrane, which protects the reference electrolyte from dilution, tends to get clogged up over time due to hard spa water, which increases sensor response time. Second, the well-defined electrolyte surrounding the reference electrode tends to mix with the spa water over time, creating a reference electrode drift. In order to resume original reference sensitivity, pH electrodes are stored in a highly acidic solution to maintain fast response times. Further, the well-defined reference electrolyte, and if possible the membrane, can be changed in an attempt to maintain spa operation that is free of drift.

While ORP and pH sensors based on the equilibrium reference electrode concept can be operated very accurately and reproducibly, it is not uncommon to see drift and response time issues if not maintained on daily basis for laboratory use or weekly basis for consumer use. Further, the sensor maintenance should be done by skilled operator such as a lab technician to avoid expensive electrode damage. As such, traditional ORP and pH sensors are considered high maintenance in continuous operation. Additionally, these temperature, flow, conductivity, ORP, and pH sensors come packaged individually or in combinations excluding one or more of above mentioned metrics, which adds to installation complexities and cost of combining individual sensors.

SUMMARY

According to one exemplary embodiment, a multi-functional sensor assembly includes an electrically non-conductive substrate defining at least a distal region, intermediary region, and proximal region that are each covered with electrically conductive traces. The proximal region is configured to be exposed to a media to be sensed and the distal and intermediary regions are configured to be protected from the media. The electrically conductive traces connect to one or more electrodes to sense one or more of alkalinity, cyanuric acid concentration, or oxidant concentration of the media.

According to another exemplary embodiment, a multi-functional sensor assembly includes an electrically non-conductive substrate defining at least a distal region, intermediary region, and proximal region that are each covered with electrically conductive traces; a printed circuit board connected to the distal region; and a housing enclosing the intermediary and distal region, and surrounding at least one end of the printed circuit board, and wherein the proximal region extends outwardly of the housing to be exposed to a media to be sensed, and wherein the electrically conductive traces connect to one or more electrodes to sense one or more of alkalinity, cyanuric acid concentration, or oxidant concentration.

In yet another exemplary embodiment, the multi-functional sensor assembly is part of a system for spa water, in which the sensor assembly has any of the components and functionalities discussed herein. Further, the sensor assembly is in fluid communication with the spa water and one or more chemical treatment components. A spa controller is operable to receive data from the sensor assembly and to control the one or more chemical treatment components to input chemicals into the spa water based on the data received.

In another exemplary embodiment, a dynamic mode of operating a three electrode setup for ORP and alkalinity documentation of a media includes establishing a first constant potential or a first constant current between a working electrode and a counter electrode and documenting a first documented potential between the working electrode and a reference electrode as a measure of ORP of a media; establishing a second constant potential or a second constant current between the working electrode and the counter electrode and documenting a second documented potential between the working electrode and the reference electrode; establishing a third constant potential or a third constant current between the working electrode and the counter electrode and documenting a third documented potential between the working electrode and the reference electrode; determining a difference between the second and third documented potentials between the working and reference electrodes as a measure of a pH of the media; and determining the alkalinity of the media from the pH of the media.

In addition or alternatively to alkalinity, cyanuric acid concentration, and/or oxidant concentration, this sensor assembly can also measure temperature, flow, conductivity, oxidation reduction potential (ORP), chloride concentration/chlorine levels, or acidity (pH). The sensor assemblies discussed herein provide an inexpensive water quality measure with a fast response time, requiring little or no maintenance and a durability on the order of months of continuous use, with minimal or no issues.

These and other features of the present disclosure can be best understood from the following specification and drawings, the following of which is a brief description.

BRIEF DESCRIPTION OF THE DRAWINGS

FIG. 2 is a perspective view of the sensor assembly of FIG. 1 installed on a printed circuit board.

FIG. 3 a top view of the PCB and sensor assembly.

FIG. 4A is a side view of the sensor assembly installed within a housing.

FIG. 4B is an end view of the sensor and housing assembly of FIG. 4 connected to a pipe.

FIG. 5 is an enlarged side view of one end of the sensor and housing assembly.

DETAILED DESCRIPTION

Figure 1:
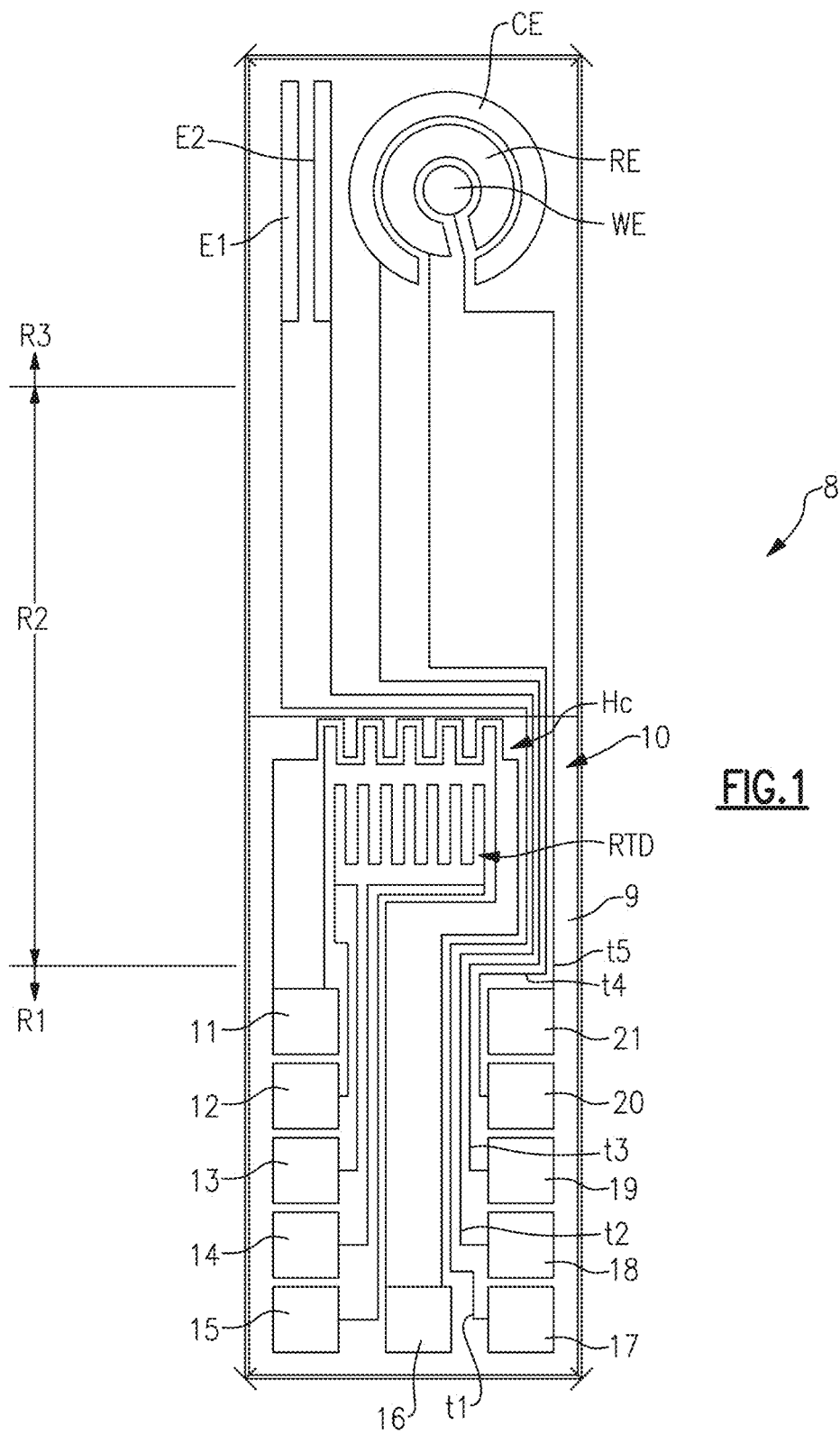
FIG. 1 shows a schematic representation of a multifunctional water quality sensor assembly according to one aspect of the disclosure.

FIG. 1 shows a schematic representation of a flow sensor assembly 8 that includes a substrate or chip body 9 and a circuit and sensor assembly 10 supported on the chip body 9 that is configured to determine temperature and flow rate for a liquid, and which is further configured to operate in a plurality of modes to sense a plurality of water conditions. In one example, the plurality of water conditions comprises at least pH (a measure of acidity or basicity of an aqueous solution), ORP (Oxidation Reduction Potential), chlorine levels, conductivity, alkalinity, cyanuric acid concentration [CYA] or cyanurate, and/or oxidant concentration $[Ox]_{tot}$. The sensor assembly thus provides lab-on-a-chip (LOAC) capability. With this lab-on-a-chip capability, the sensor assembly can contain, in one chip, the components to measure various water conditions and report those water conditions as data. The data can be reported wirelessly and/or with the use of various indicators and alarms, to computer systems that store and/or regulate the spa water, spa users, and/or spa maintenance providers when further chemicals and/or spa maintenance is needed.

The chip body 9 is significantly smaller than prior configurations and is capable of determining temperature, flow rate, pH, ORP, conductivity, alkalinity, cyanuric acid concentrations, oxidant concentrations, and chlorine levels in an accurate manner. In one example, the chip body 9 comprises a single piece substrate that is approximately 4.0 mm by 1.0 mm by 0.5 mm or less. In one example, the substrate or chip body 9 is electrically non-conductive such as, but not restricted to, silicon or glass or an organic polymer such as polyimide, PE or PP or PTFE.

In one example, the chip body 9 is coated using lithographic technology in patterns with a conductive materials such as platinum and titanium and alloys thereof. The resulting sensor assembly 8 has three regions: (1) a first or distal region R1 at a distal end, which serves for external connection; (2) a second region R2, which is an intermediary region and hosts temperature and flow circuitry that are not exposed to a medium to be sensed; and (3) a third region R3 at a proximal end and which hosts electrodes for direct media contact sensing of conductivity, ORP and pH.

The sensor assembly 8 comprises several separate platinum (Pt) circuits, leads, electrodes and pads deposited, in thickness of about 1 μm, on an electrical insulating silicon (Si) substrate as shown in FIG. 1. One circuit $H_c$ acts as resistive heating element and includes segments 11 and 16. Other circuits act as a temperature sensor, referred to as a RTD, and include segments 12, 13, 14 and 15. First and second conductivity electrodes $E_1$, $E_2$ act as a conductivity sensor and include pad segments 17 and 18. Finally, three segments 19, 20 and 21 correspond to the combined ORP and pH sensor electrodes. Pad segment 19 is connected to the pH and ORP sensor counter electrode CE, pad segment 20 is connected to the reference electrode RE, and pad segment 21 is connected to the working electrode WE.

The leads, circuits, electrodes, and bonding pads are laid out in one of the three regions on the chip body 9. The proximal region, or third region R3, holds the pH, ORP and conductivity electrodes CE, RE, WE that are connected to segments 19, 20, 21, and which all are exposed to the medium to be sensed. The intermediary region, or second region R2, holds the temperature and flow circuitries that are entirely overpotted inside a housing. The distal region, or first region R1, holds leads to the intermediary circuits and proximal electrodes through wire bonding pads for external connectivity.

The relatively small size of the sensor assembly 8 is best shown in FIGS. 2-3, which show the chip body 9 mounted to a printed circuit board (PCB) 22. The PCB 22 has a first end 24 and a second end 26. In one example, the chip body 9 is mounted to an extension portion 28 extending outwardly of the first end 24. A connection jack 30 for electrical connections is mounted to the second end 26. The chip body 9 is bonded, e.g. glued, to the, PCB 22 and the chip pads or segments 11-21 are wire bonded to the PCB 22 for preliminary signal conditioning and external connection.

FIG. 3 shows the PCB 22 with the chip body 9 having the third, or proximal, region R3 extending beyond the extension portion 28 of the PCB 22. The chip and board assembly is inserted in a housing 32 (FIGS. 4A-7) that is potted and sealed with resin in order to establish a barrier against media ingress (water) to the first R1 and second R2 regions while exposing region R3 to the flow media. The assembled sensor is interfacing with support electronics for powering, excitation patterns, and sequencing and signal conditioning for sensor output display.

Figure 6:
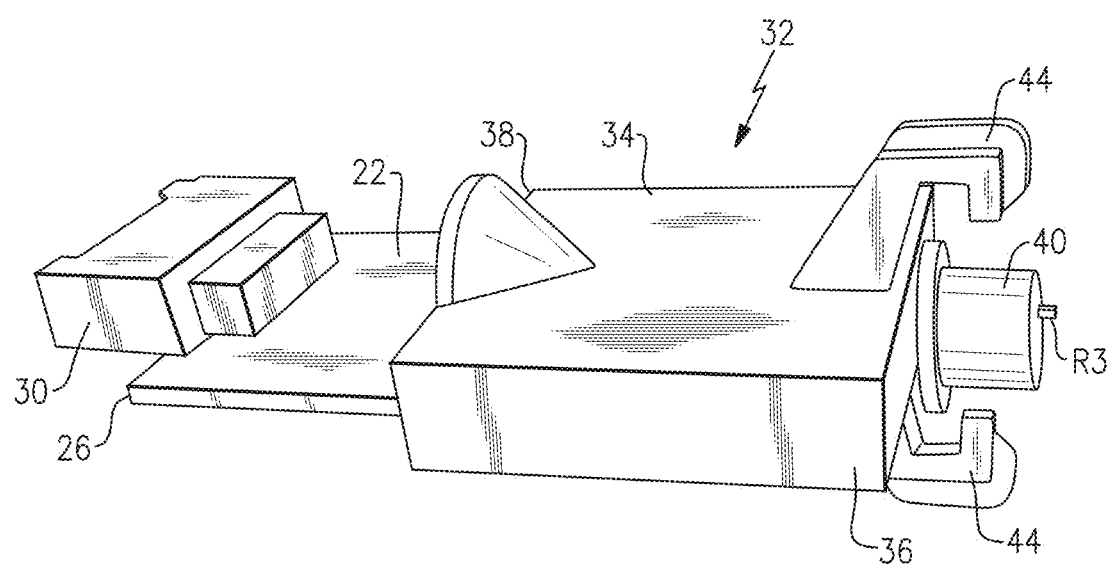
FIG. 6 is a side view of an assembly including the housing, sensor, PCB, and electrical connector.

FIG. 4A shows the housing 32, which comprises a body portion 34 having a first end 36 and a second end 38. The first end 36 includes a reduced diameter portion 40 extending axially outward and which includes an opening 42 (FIG. 5). The third region R3 extends through this opening 42 and axially beyond the reduced diameter portion 40 as shown in FIGS. 4A and 5-6. The reduced diameter portion 40 includes attachment features 44 that couple the housing 32 to a tube 46 through which the medium flows as shown in FIG. 7.

In one example, the attachment features 44 comprise arms that fit around a flange mount 48 formed on the tube 46; however, other attachment structures could also be used. The tube 46 defines an open inner conduit 50 that defines a flow path for the flowing medium. When the housing 32 is coupled to the tube 46, the third region R3 extends into the flow path as shown in FIG. 4B.

Figure 7:
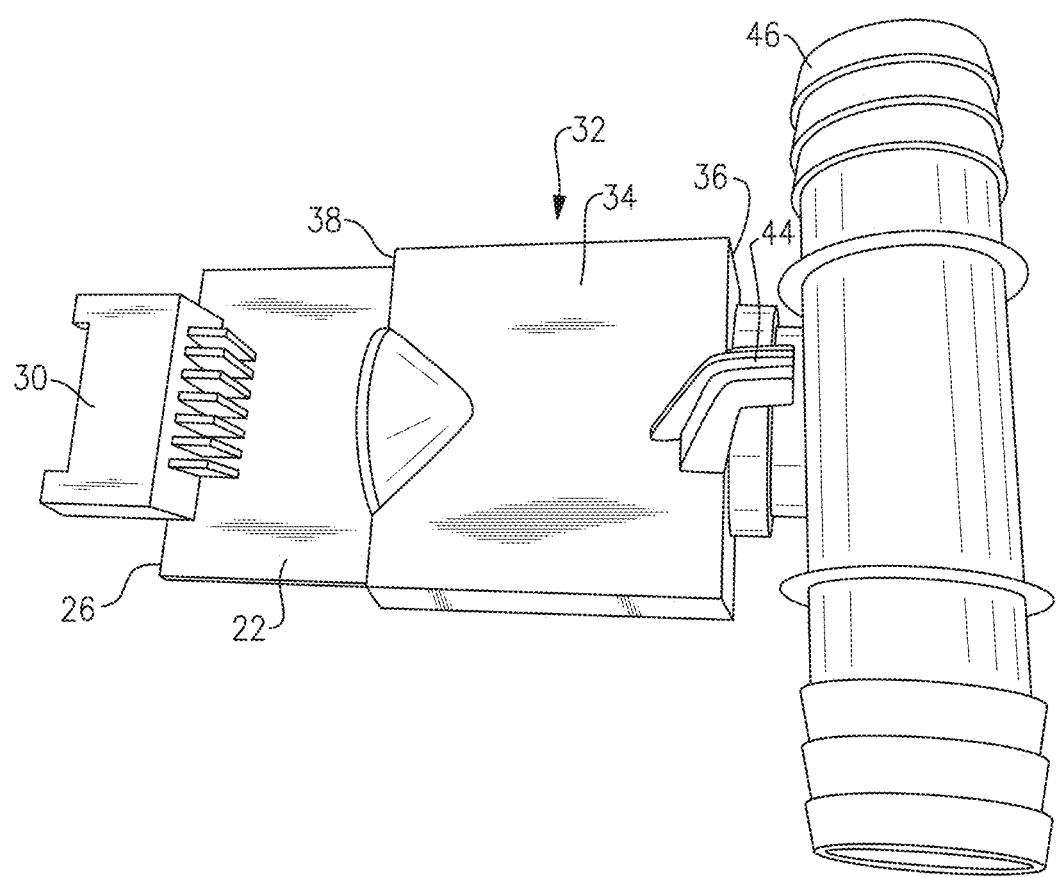
FIG. 7 is a top view of the assembly of FIG. 6 connected to a pipe.

The PCB 22 extends outwardly of the second end 38 of the housing 32 (FIGS. 6-7). The second end 26 of the PCB 22 is thus exposed such that the connection jack 30 can be coupled to a connection interface 52 (FIG. 3) on the PCB 22.

Traces $t_1$, $t_2$ connect pad segments 17, 18 to the conductivity electrodes $E_1$, $E_2$, and traces $t_3$, $t_4$, $t_5$ connect pad segments 19, 20, 21 to the counter electrode CE, reference electrode RE, and working electrode WE. The traces $t_{1-5}$ extend across the intermediary region R2 and into the third region R3. As such, portions of the traces $t_{1-5}$ are exposed to the flowing water. One will realize that the water exposed portion of these traces $t_{1-5}$ differs in area and relative orientation but can be interchanged such that any three electrodes (CE, RE, WE) can be configured for pH, ORP and chlorine sensing while any two electrodes $E_1$, $E_2$, can be configured for conductivity sensing. These electrodes can also be configured to measure or sense alkalinity, cyanuric acid, and various oxidant concentrations, each directly and/or indirectly from other measurements. For the same reason, three electrodes can be configured for all the aforementioned sensing jobs: conductivity, pH, ORP, alkalinity, cyanuric acid, oxidant concentration, and chlorine separated by mode of operation in time or sequence or overlapping. For example, the conductivity mode of operation is done via documentation of $I_{rms}$ resulting from a 6 kHz, 0.25V signal that for all practical purposes can, by overlaying a DC signal, be used for documenting pH, ORP and chlorine levels. An analogy would be signals carrying radio transmissions where the audible portion of the signal is carried as perturbations of a carrier wavelength such as a signal for a radio station.

One purpose of the disclosure is to create a multi-functional sensor assembly 8 with combinations of temperature, flow conductivity, pH, ORP, alkalinity, cyanuric acid, various oxidant, and chlorine sensing capabilities and associated sensor operation modes for general purpose and low cost sensing for commercial plumbing related applications. The sensor assembly 8 utilizes low cost Si chip or glass substrates and utilizes standard processing for high volume manufacturing of microchips in combination with unique mode of control allowing for sensing. This will be discussed in greater detail below.

The temperature is derived from the resistance of the sensor circuitry. The concept of measuring temperature with RTD is well known in the art. However, the subject disclosure discusses a heat pulse technique to determine both temperature and flow using the same single sensor circuit. The flow is derived from the temperature sensor when the heating element 11, 16 is powered. Essentially, the power gives rise to a temperature increase that is dissipated. The heat dissipation is a function of the cooling rate of the chip that is inversely proportional to the flow velocity of fluid passing the sensor. The peak temperature can be translated into a flow.

In some cases, the temperature rise by way of the heating element is muted, at least in part, by heat transfer to the exposed media. This heat transfer can be tempered or minimized by a stationary layer of media (e.g. spa water) surrounding the chip. This adjacent layer of stationary media is a diffusion layer. The thickness of this diffusion layer is higher when the velocity of the adjacent or surrounding media is low, and lower or thinner when the velocity of the surrounding media is high.

Several advantages are achieved by operating the heating element in pulsed power loads. First, the overall power needed to operate the flow function is reduced. Second, the chip is protected from overheating in situations where the cooling rate is low, i.e. no flow. Third, a large response is provided in short time span. By reducing the thermal mass of chip, the response time can be reduced to range of seconds and sub-seconds. Finally, temperature measurement is enabled in a "power off mode" and flow is enabled in a "power on mode," and consequently only one temperature sensor is needed for flow and temperature sensing.

By reducing the thermal mass of chip, the response time can be reduced to range of seconds and sub-seconds. A fast response can be achieved by using a substrate with high thermal conductivity properties such as silicon. Similarly the power needed to provoke such response is lowered by using a substrate with high thermal conductivity such as silicon (see examples 1, 2 and 7 below).

Figure 8:
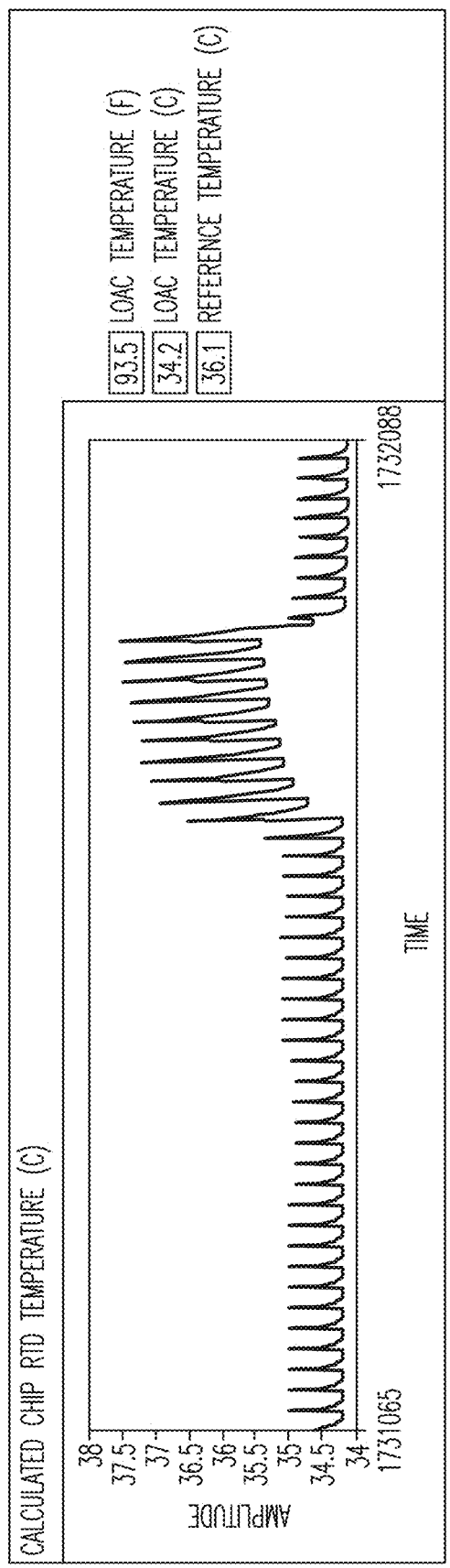
FIG. 8 shows amplitude v. time for a calculated chip RTD temperature.

FIG. 8 shows sensor response during flow excursions. FIG. 8 shows amplitude v. time for a calculated chip RTD temperature and thus shows a LOAC temperature response following a change in flow. FIG. 8 shows the LOAC response in temperature to repeated heat pulses to heater circuit 11, 16 of duration of 200 ms every 1000 ms creating distinct peak temperatures and base or valley temperatures. Peak temperature is inversely related to flow velocity and flow.

Figure 9:
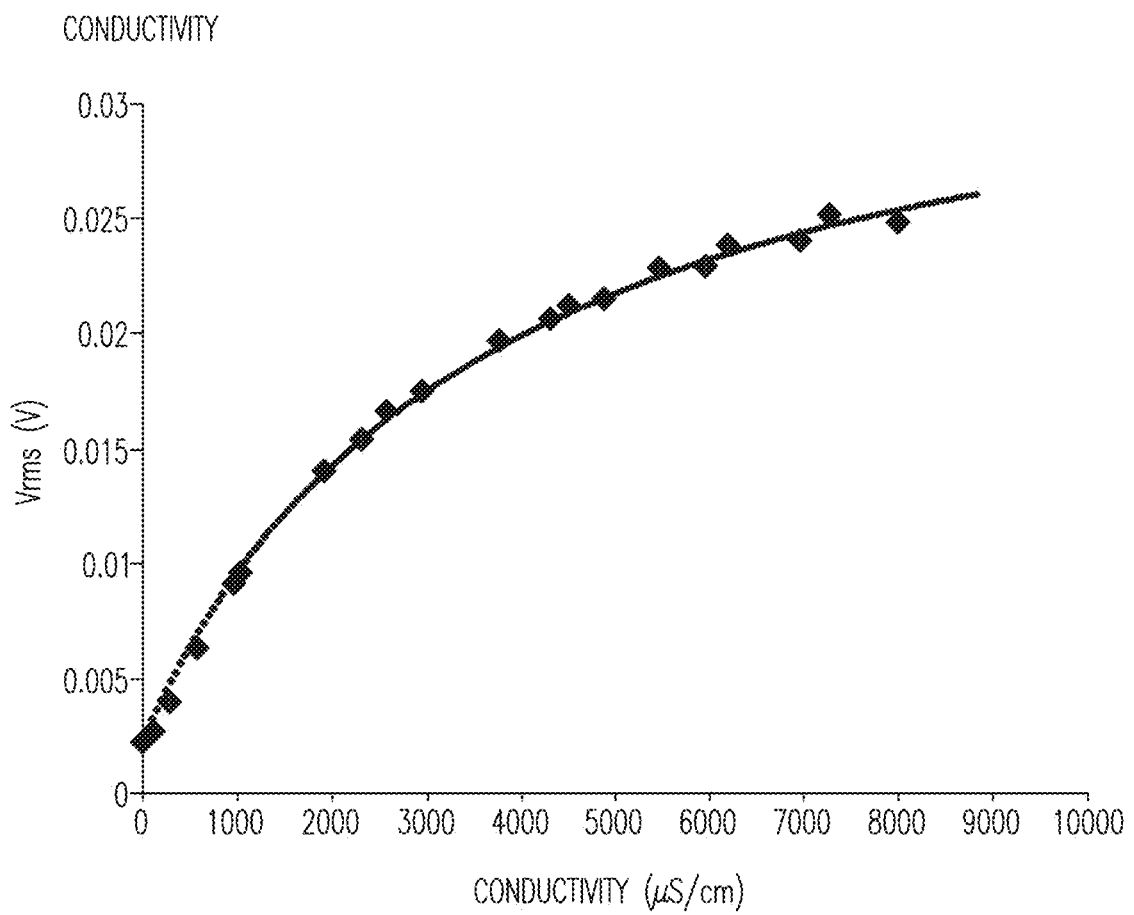
FIG. 9 shows $V_{rms}$ v. Conductivity.

Conductivity sensing is done by documenting the DC resistance of two or more water immersed wires operated at an AC frequency. Sometimes conductivity is translated into total dissolved solids, requiring a temperature correction of conductivity to produce reliable results. Example 3 below describes how this is done, and FIG. 9 shows the sensor response to exposure to waters of increasing conductivity created by sodium chloride additions. More specifically, FIG. 9 shows $V_{rms}$ v. Conductivity, and depicts LOAC sensor response following a change in conductivity caused by adding sodium chloride to the spa chemistry, displayed along with calibrated reference conductivity measurement.

In one example, the following temperature and flow algorithms were used:

$T = mV + b$

This algorithm states that temperature is a linear function of a voltage drop over a resistor given a known current. Sensors based on this temperature sensitive resistor method are broadly referred to as RTD.

$$F_{(T)} = a\left(1 + \left|\frac{dT}{dt}\right|\right)^i \left(1 + \frac{\Delta T_{cal}}{T_{cal}}\right)^m \Delta T_{pulse}^n + b$$

This algorithm inversely correlates the flow with the temperature increase as documented by sensor induced by a power load to a heater circuit located close to the sensor. Sensors documenting flow through cooling rate are known as anemometers. The complexity of the above algorithm is due to the fact that a voltage pulse is being used, which does not give a constant power with temperature, necessitating the incorporation of correction factors. One of the inventive features is the use of this pulsed power which allows the use of the RTD to document both flow and temperature.

Conventional electrochemical theory on sensors is based on equilibrium type of solutions, i.e. reference electrodes in designed electrolytes separated from medium of interest by high resistivity salt bridge to which a sensor electrode is referred for obtaining absolute values. The sensor electrode may be covered with ion selective membrane for increased sensitivity for specific ions.

The three electrode type of configuration shown in FIG. 1 is adopted for advanced characterization in disciplines like cyclic voltammetry and impedance spectroscopy. FIG. 1 shows the counter electrode CE, reference electrode RE, and working electrode WE connected to pad segments 19, 20 and 21. The equilibrium approach traditionally teaches that when using a silver chloride reference electrode in dedicated electrolyte, polarization is established between the working electrode WE and the reference electrode RE while running current between the working electrode WE and the counter electrode CE thereby generating characteristics for the working electrode WE. In this configuration, monitoring equilibrium potential between the working electrode WE and the reference electrode RE, also called open circuit voltage, OCV, will produce a potential that can be translated into an ORP after correction for the silver chloride reference standard potential. Similarly, covering the working electrode WE with an ion selective film such as Nafion and documenting the OCV between the working electrode WE and the reference electrode RE will produce a potential dominated by proton activity, translatable to pH with appropriate correction for the reference electrode.

These equilibrium approaches are highly effective in creating desired results however they have shortcomings in terms of time, cost and durability.

For example, a significant amount of time is required in order to establish equilibrium in a system operated at high resistance—often several minutes. Also, cost significantly increases when manufacturing physically complicated reference electrodes and highly specialized membranes for sensor electrodes. Further, the durability of the equilibrium approach is limited because reference electrodes are operated in inherently non-equilibrium environments requiring maintenance for sustained operation, and because ion-selective membranes have a tendency to foul up, producing drift and delayed time response.

Using the dynamic sensor approach overcomes these limitations. The dynamic approach can provide a fast, durable sensor that exceeds months in continuous use with little or no maintenance and minimal or no issues (e.g. drift or calibration). The dynamic approach determines pH, ORP, alkalinity, cyanuric acid concentrations, and chlorine levels using a single dedicated three electrode sensor. As discussed above, FIG. 1 shows the counter electrode CE, reference electrode RE, and working electrode WE connected to pad segments 19, 20 and 21. The approach polarizes (draws current) between the working electrode WE and the counter electrode CE and follows the temporal development in potential between the working electrode WE and the reference electrode RE, which is a response that is ORP and pH dependent.

Figure 10:
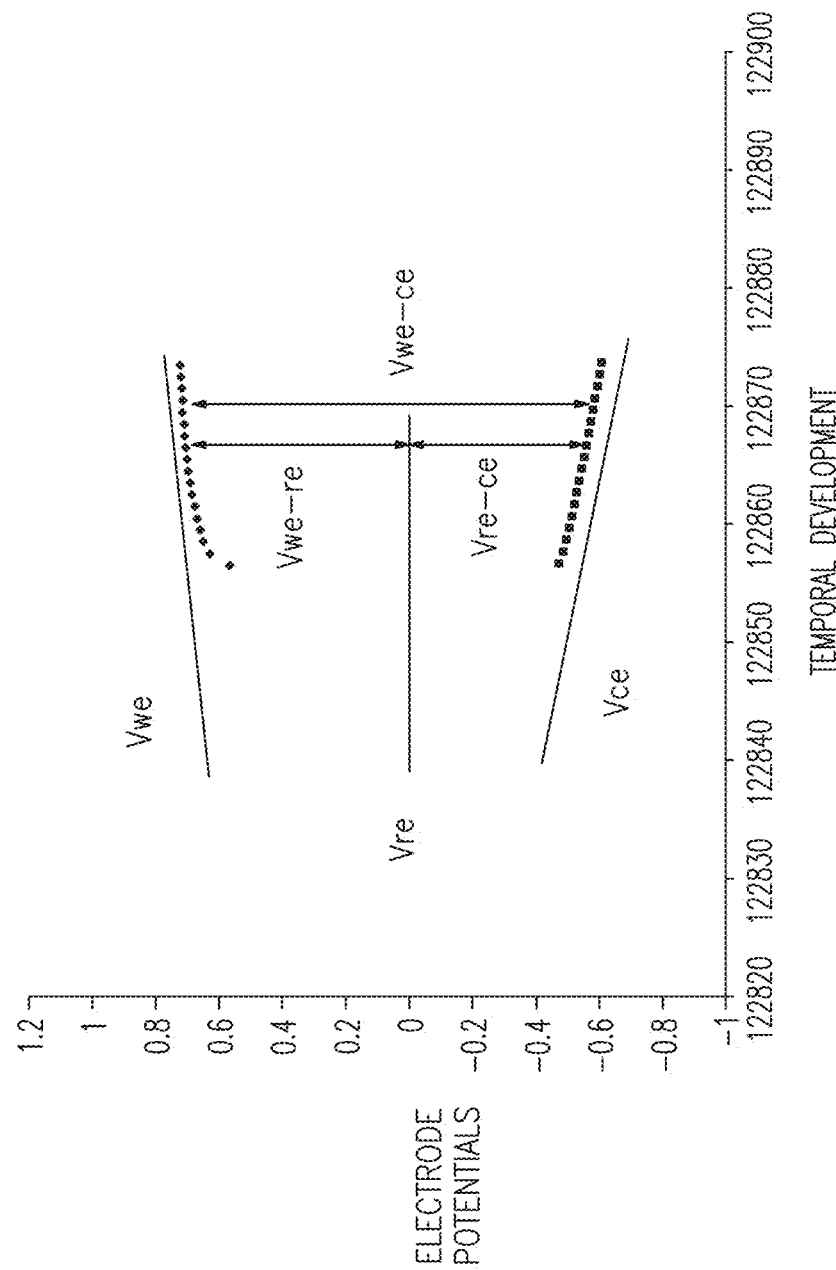
FIG. 10 shows the LOAC sensor response following a polarization event in time.

Polarization between the working electrode WE and the counter electrode CE, $V_{WE-CE}$, creates a potential between working electrode WE and reference electrode RE. $V_{WE-CE}$, is dependent on the degree of polarization and the ORP of the solution. Such a polarization is shown in FIG. 10. FIG. 10 shows the LOAC sensor response following a polarization event in time. The graph shows temporal development (horizontal axis) of electrode potentials (vertical scale) derived from running the three electrode sensor at 600 nA between the working electrode WE and the counter electrode CE Pt electrodes with the floating the reference electrode RE. The various potentials $V_{RE}$, $V_{WE-CE}$, $V_{WE-RE}$ and $V_{RE-CE}$ are shown on the graph. The solid lines are introduced to guide the eye.

Figure 11:
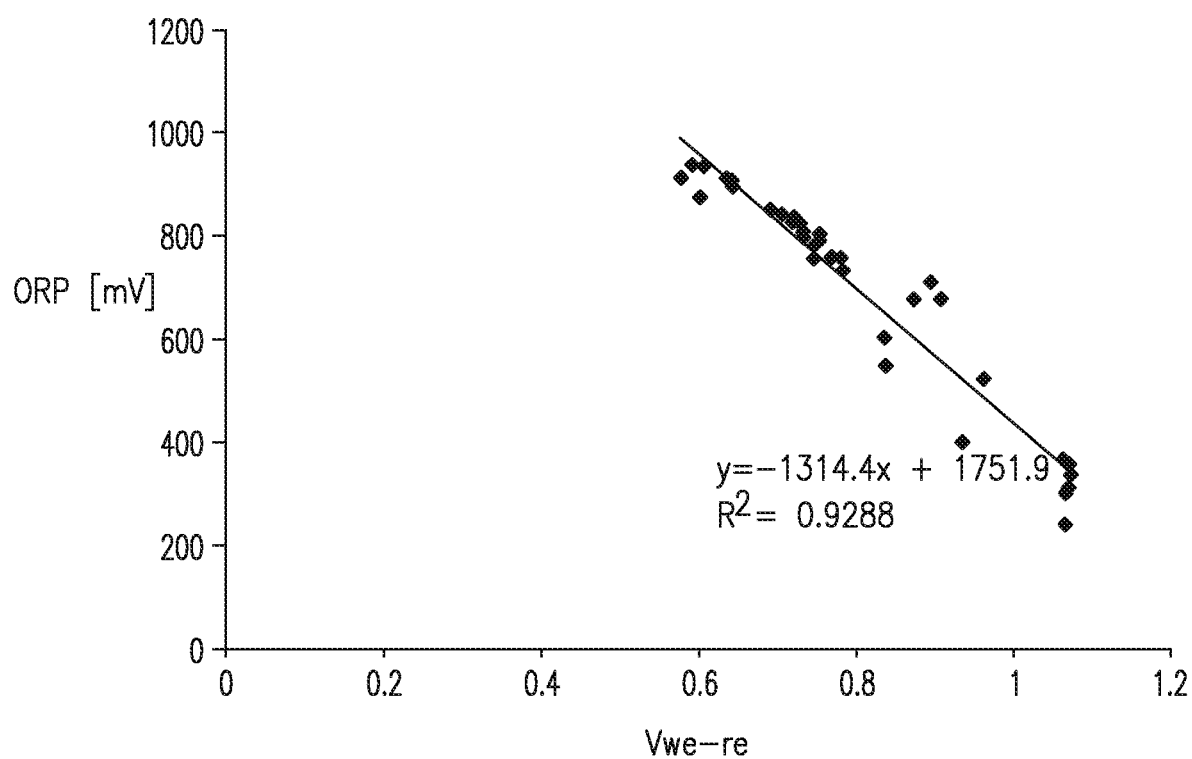
FIG. 11 graph shows LOAC sensor ORP responses following a change in ORP.

Practical experiments have shown that changing the ORP of the solution for any given polarization exceeding approximately 0.7 V is directly correlated to the $V_{EW-ER}$ potential observed between working electrode and reference electrode. Such an ORP relation is shown in FIG. 11 for $V_{WE-RE}$ vs ORP. The FIG. 11 graph shows LOAC sensor ORP responses following a change in ORP caused by adding sodium DiChlororCyanurate (DCCy), sodium chloride, sodium bisulfate, sodium bicarbonate to the spa chemistry—displayed along with calibrated reference ORP measurement. In practice one should not exceed 1.5 V polarization for extended time as hydrogen gas evolution will create time fluctuations in the electrode area and provoke a noisy relation.

Figure 12:
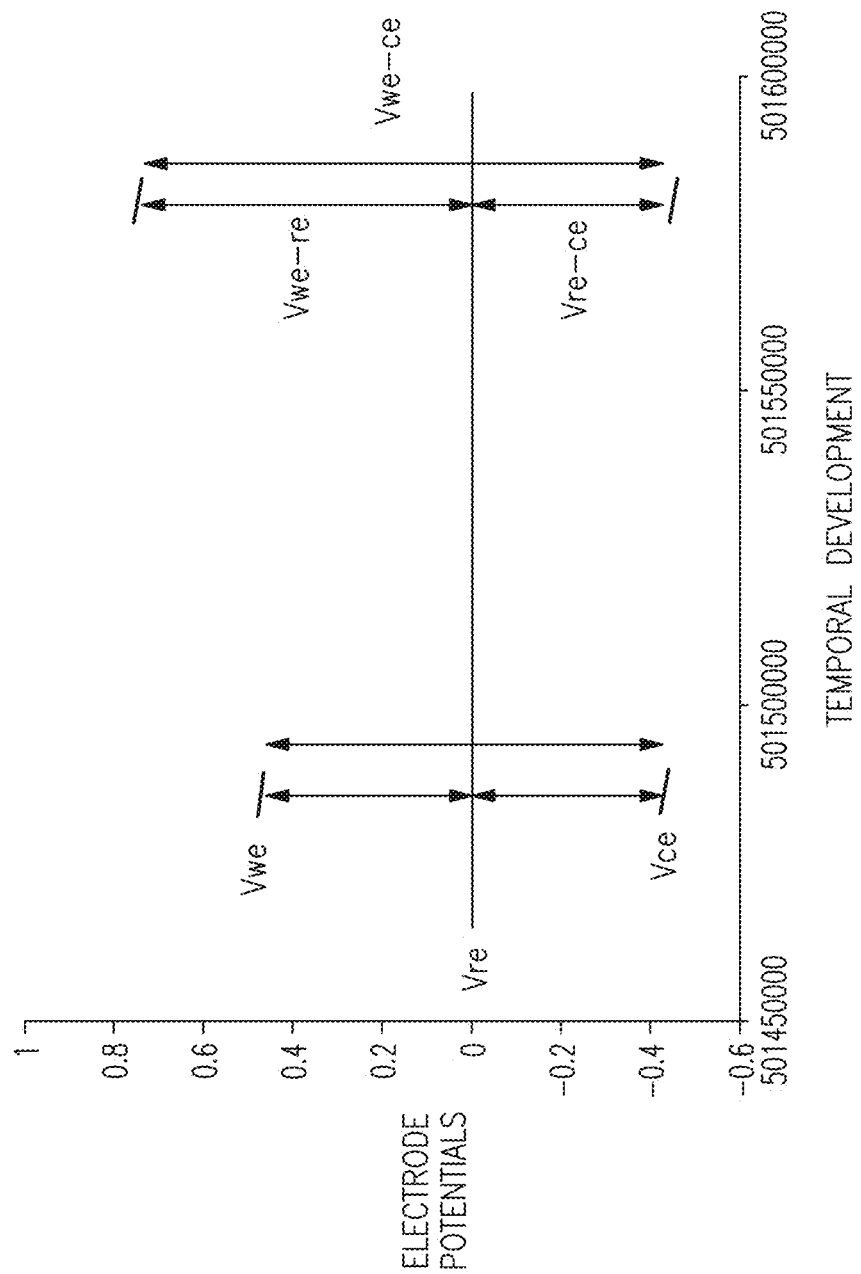
FIG. 12 shows the LOAC sensor response following a polarization event in time.

FIG. 12 shows the LOAC sensor response following a polarization event in time. The graphs shows temporal development (horizontal axis) of electrode potentials (vertical scale) derived from running the three electrode sensor at 0.9 V and 1.2 V between the working WE and the counter CE Pt electrodes with floating the reference electrode RE.

Figure 13:
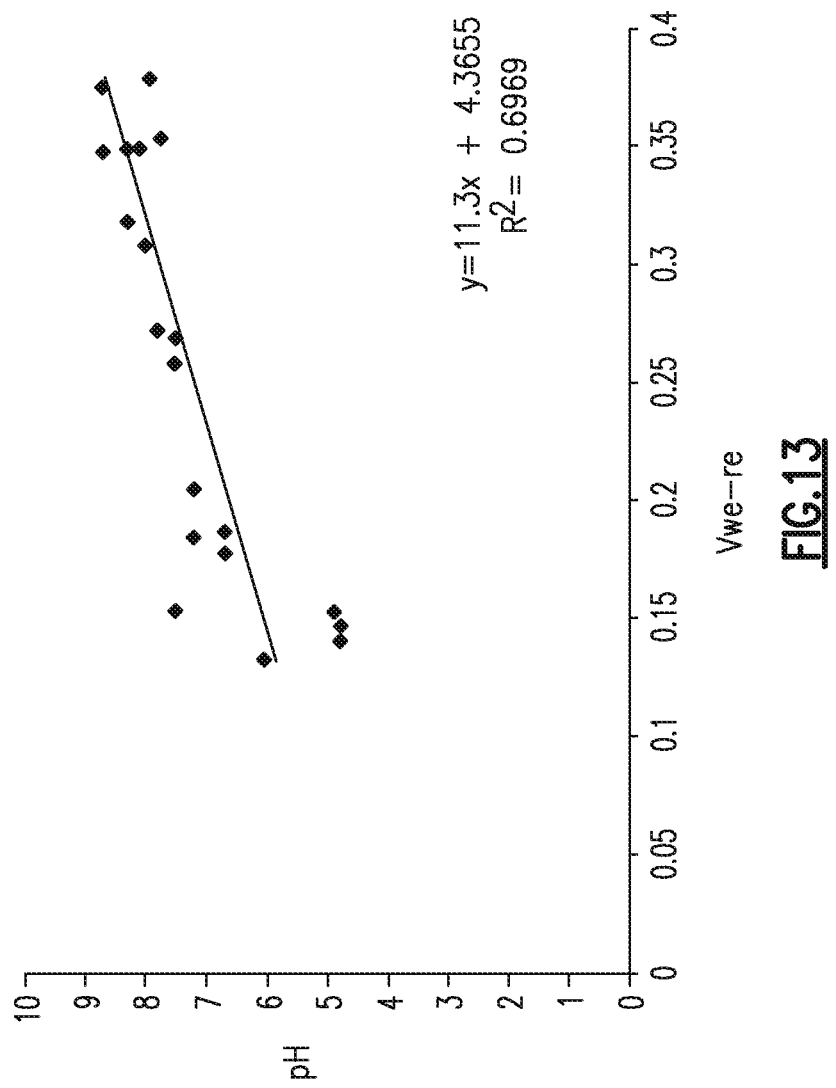
FIG. 13 shows pH vs $\Delta V_{WE-RE}$ for a high chloride result.
Figure 14:
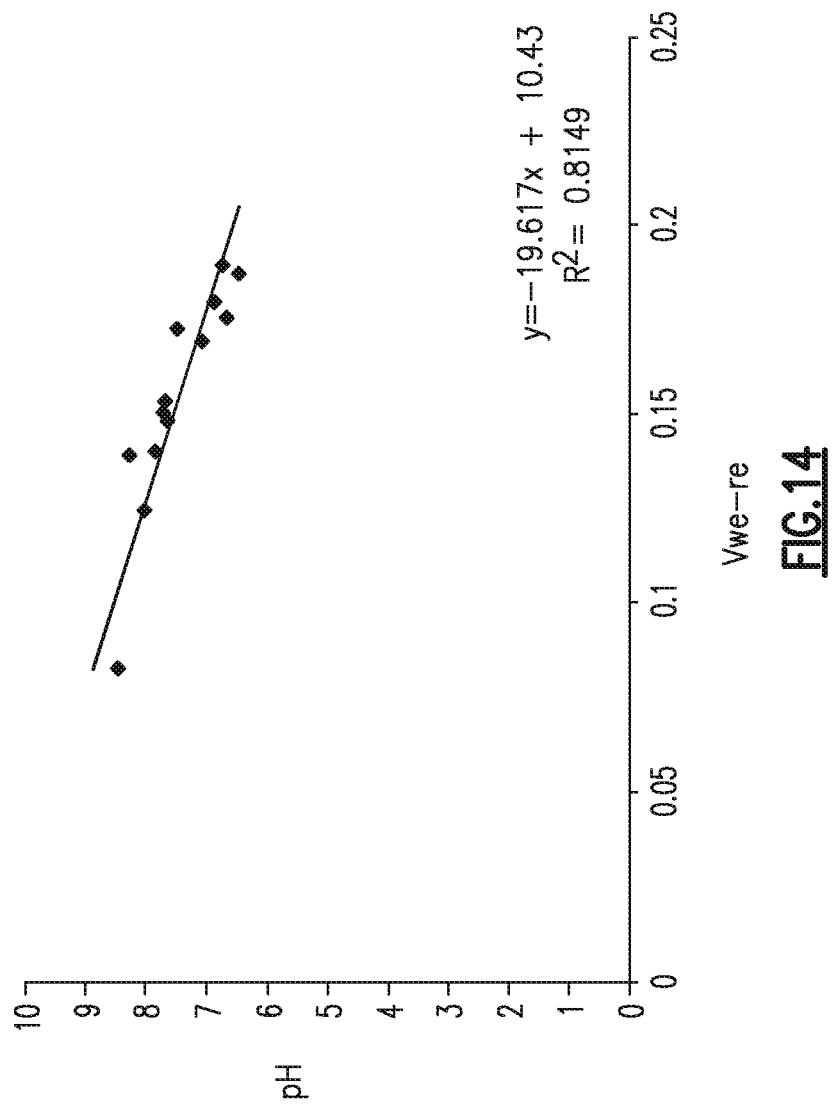
FIG. 14 shows pH vs $\Delta V_{WE-RE}$ for a low chloride result.

A change in the $V_{WE-CE}$ polarization gives rise to a change in $V_{WE-RE}$. Practical experiments have shown that, focusing on the interval of 0.7 V-1.5 V for $V_{WE-CE}$ potential, a change of 0.3 V, $V_{WE-CE}$, from approximately 0.9 V to 1.2 V gives rise to a change in $\Delta V_{WE-RE}$ that correlates with pH. FIGS 13 and 14 show $\Delta V_{WE-RE}$ VS PH for correlations in chloride high solution and chloride low solution.

Specifically, FIG 13 shows the LOAC sensor pH responses following a change in ORP caused by adding DCCy, sodium chloride, sodium bisulfate, sodium bicarbonate to the spa chemistry—displayed along with calibrated reference pH measurement. Chloride high concentration, i.e. NaCl, is more than 1000ppm. FIG 14 shows the LOAC sensor pH responses following a change in ORP caused by adding DCCy, sodium bisulfate, sodium bicarbonate to the spa chemistry—displayed along with calibrated reference pH measurement. Chloride low concentration, i.e. NaCl, is less than 200ppm.

Figure 15:
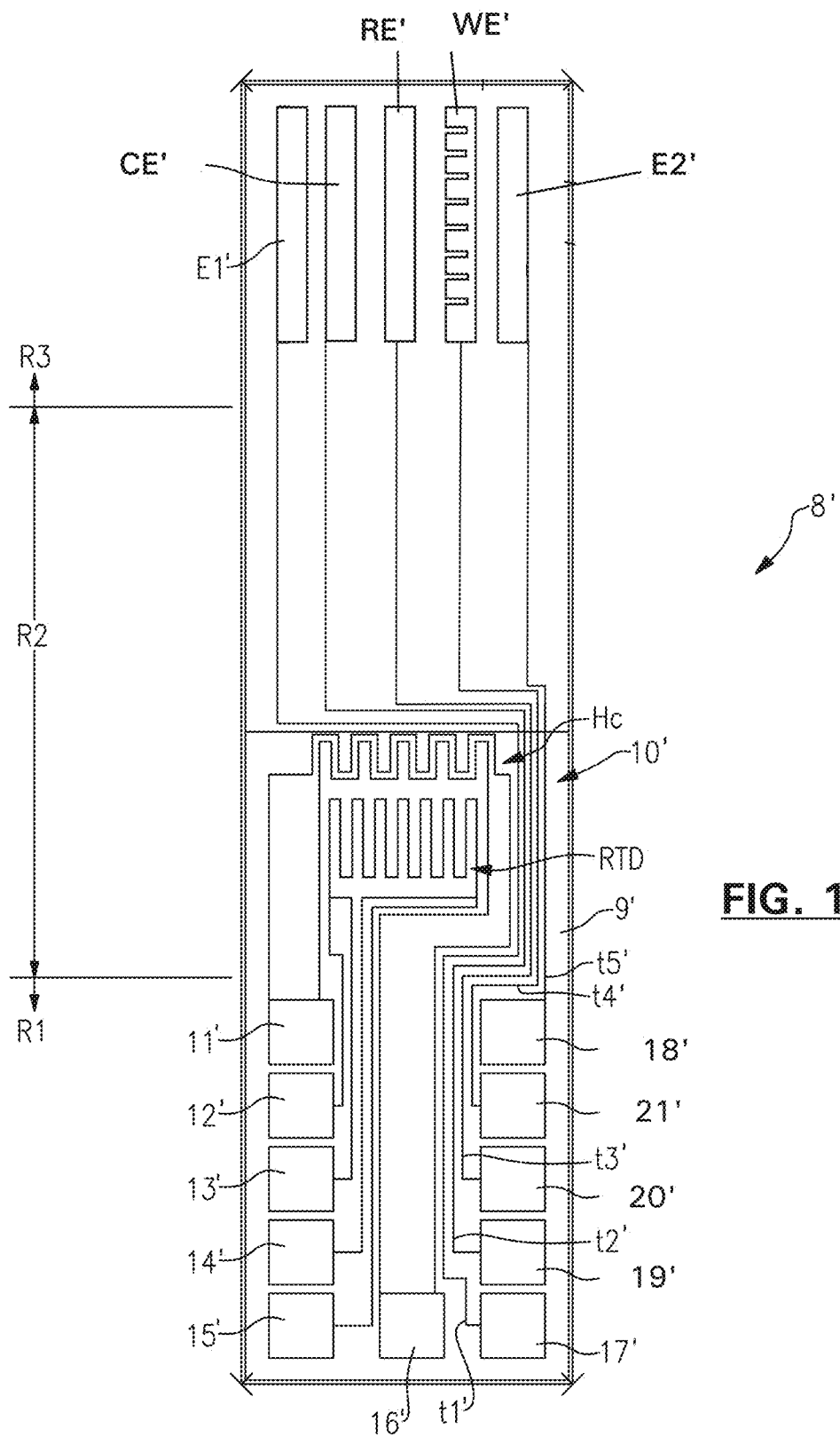
FIG. 15 shows a schematic representation of a multifunctional water quality sensor assembly according to another aspect of the disclosure.

FIG. 15 shows an alternative layout of a chip body 9' with a circuit and sensor assembly 10' supported on the chip body 9'. In FIG. 15, a flow sensor assembly 8' is the same as in FIG. 1, with the exception of a different configuration for the electrodes that measure conductivity and ORP/pH. Reference numerals are indicated with a prime (') symbol in FIG. 15. Pads 11', 12', 13', 14', 15', and 16' are similar in placement and functionality to pads 11-16 in FIG. 1.

In FIG. 15, five electrodes are positioned to contact the media in a linear arrangement. In this example, the conductivity electrodes (E1', E2') are on the outer ends or edges of the chip body 9', with the CE', RE', and WE' positioned in between the conductivity electrodes. Each electrode is shown in a linear arrangement. In this example, five electrodes are arranged in a row so that a first electrode is a first conductivity electrode (E1'), a second electrode is a counter electrode (CE'), a third electrode is a reference electrode (RE'), a fourth electrode is a working electrode (WE'), and a fifth electrode is a second conductivity electrode (E2').

The conductivity electrodes (E1', E2') are connected to pads 17' and 18', respectively. Similarly to FIG. 1, E1' connects to pad 17' via trace $t_1'$, and E2' connects to pad 18' via trace $t_5'$. The ORP/pH electrodes (CE', RE', WE') connect to pads 19', 20', and 21', respectively. CE' connects to pad 19' via trace $t_2'$. RE' connects to pad 20' via trace $t_3'$. WE' connects to pad 21' via trace $t_4'$. This linear and side-by-side arrangement of the electrodes could give the advantage of all or substantially all portions of each electrode being able to contact the flowing media before any or substantially any portions of the adjacent electrodes contact the flowing media. All electrodes can be spaced equidistantly from each other, or they can have some other type of spacing.

To measure conductivity, CE' can also be referred to as $RE_1$ and RE' can also be referred to as $RE_2$. The two conductivity electrodes (E1' and E2') are conductivity excitation electrodes. As an alternative approach to measuring conductivity with two electrodes (E1, E2) as discussed herein, the sensor can have a four electrode (E1', E2', $RE_1$, $RE_2$) set up.

To measure ORP/pH, a three electrode system includes the CE', RE', and WE'. This three electrode system is the same as shown and discussed in FIG. 1 with the CE, RE, and WE, with the exception of the placement and geometry of the electrodes relative to the conductivity electrodes.

In order to measure the pH accurately, the current density can be varied to avoid pH perturbation caused by galvanostatic operation. In one aspect, the electrodes have small volumes of solution immediately adjacent to and covering the electrodes. For example, the anolyte and catholyte are very small volumes immediately adjacent to the anode and cathode, respectively. The thickness of this volume is a diffusion layer and is a variable of bulk flow velocity. In one example, this thickness has a value of 30-100 μm, including all ranges, subranges, and values therebetween. The diffusion layer thickness can be established via simulations adopted from rotating electrode theory. At any given pH the anolyte will experience a pH reduction and the catholyte will experience a pH increase as a function of a galvanostatic current.

Specifically to measure pH, the sensor described herein can determine the dynamic pH in two galvanostatic steps. While not wishing to be bound by any particular theory, the inventor(s) believe that pH can be found as the second derivative if potential with current. It may also be possible to measure pH using a first derivative approach. In order to measure pH accurately, it may be beneficial to also know the oxidant and buffer concentrations of the media.

In addition to finding pH using the methods discussed herein, it is also possible to find the alkalinity of the solution using the described sensor assembly. The alkalinity is defined as the sum of anions derived from weak acids measured as a molar concentration. Alkalinity is a measure of how much acid a solution can take up when titrated by a strong acid, a measure of buffer capacity. While not wishing to be bound by any particular theory, the ions typically referred to are bicarbonate, carbonate, borate, water, phosphate, hydrogen phosphate, silicate, cyanurate corrected for acids like protons and bisulfate. Knowing the pH can allow prediction of the alkalinity of the solution.

The sensor assembly and system described herein can also be used determine the cyanuric acid concentration and other buffers in the system. Cyanuric acid is often added to the media, and it can dissipate. This sensor assembly allows a determination of the cyanurate and/or cyanuric acid concentration currently in the media. While not wishing to be bound by any particular theory, it may be possible to determine the cyanurate concentration, a function of total cyanuric acid, by determining the dichloro and/or trichloro species in the media. In an alternative approach, it may also be possible to determine the cyanurate concentration in the media from the conductivity at a known pH. Once the cyanurate concentration is known, it is also possible to use the cyanurate concentration to determine alkalinity.

The sensor assembly and system described herein can also be used to determine the oxidant concentration of the water (e.g. spa water). While not wishing to be bound by any particular theory, it is possible that by applying a negative potential, $E_{R-WE}$, to the WE relative to the RE, the resulting current, $I_{WE}$, is a measure of the oxidants concentration, C, available at the electrode surface for reduction. The surface concentration changes as result of the reduction, and a concentration gradient develops. At high flow velocities with thin and constant diffusion layers, this sensor can give highly sensitive measurements with a short response time.

In any of the sensor configurations described herein, it is possible to configure the WE, or any of the other electrodes described, such that it experiences periodic polarity reversals for cleaning and re-establishing a nascent or original state of the electrode surface to clean the surface from precipitation. This precipitation may be caused by sensitivity of the electrode to oxidants in the solution.

It will be appreciated that the spa water or media has various physical and chemical parameters, including chemistry related to the conductivity, oxidation reduction potential (ORP), acidity (pH), alkalinity, cyanuric acid concentration, or oxidant concentration, and physical parameters relating to flow and temperature.

In addition to the various spa water or media parameters/qualities that the sensor assembly can determine, this disclosure will now discuss in further detail the types of systems that include or are connected to the sensor assembly. For example, the LOAC sensor assembly attributes discussed herein can be carried out on a fully closed loop system, which allows the sensor assembly and its various system components to automatically measure/regulate and control chemical levels with no or minimal intervention by any spa managers. These include various optional components, such as sensors, circulations pumps, chlorine generator, liquid and/or dry chlorine reservoir, acid and base reservoir, dosing pumps and apparatus, and/or flow control elements. The components can also include attributes to detect flow problems, such as low flow caused by a plugged filter and/or no flow caused by malfunctioning or broken circulation parts (e.g. pumps). These components assist in automatically regulating the water quality from the sensor feedback. All or some of the components can be wirelessly or directly connected to each other, and can be portable.

The LOAC sensor assembly can include various user proximity based functions to manage water parameters closely when the user is close to the water system (e.g. using a spa frequently) and to manage water parameters more loosely when the user is away from the water system (e.g. on a vacation). The LOAC sensor assembly can operate entirely remotely, remotely controlling a spa and allowing access to spa water care values remotely.

Figure 16:
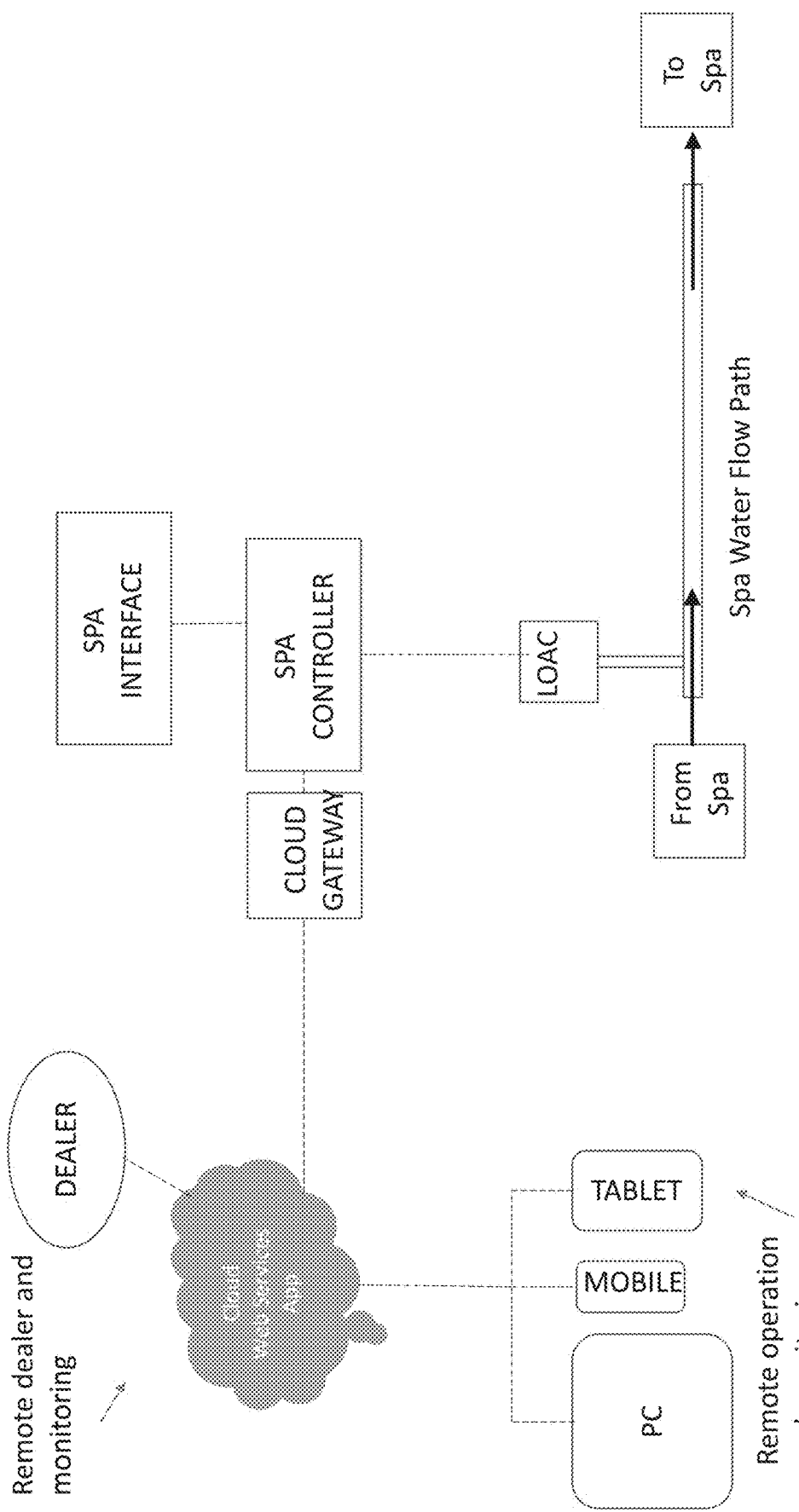
FIG. 16 depicts a block diagram of a first exemplary system including the LOAC sensor.

FIG. 16 depicts one system or assembly of operating the LOAC sensor. The LOAC sensor can intake water or media from the spa, analyze the media according to the characteristics described herein, generate data about the media quality and/or characteristics, and recirculate the media to the spa. The LOAC sensor module may be installed in the spa plumbing. Typically, the LOAC sensor is installed in plumbing which houses the heater so that the water flow can be monitored to ensure that the heater activates when there is flow. The LOAC is electrically connected and interfaced with the spa controller and feeds back data on temperature, flow, conductivity, pH, and ORP. Other data including chlorine level, alkalinity, and hardness can be pending.

A spa controller controls the LOAC functionality. The spa controller is the central hub of the system. All components are connected (directly or wirelessly) to the controller. The spa controller is connected to a spa user interface that allows the spa user to set, select, and control various LOAC features. The LOAC data is displayed to the spa user via the spa interface panel. In this example, all chemical modifications to the spa are performed manually by the spa user in light of the data received from the system.

The spa can be equipped with an internet access point or cloud gateway. The spa controller can also be connected to the cloud gateway that connects the LOAC sensor to the internet so that it may be accessed by various third parties (e.g. the spa dealer). A spa dealer can monitor the spa and make operational changes and/or be alerted to a service need, such as a need for additional chemicals. The spa data can also be pushed to the internet and/or could and accessed via internet connected devices such as computers, phones, and tablets via an application (app). The user or another third party can access the spa, operate the spa remotely, and make changes as needed. The various spa users and the related third parties can be collectively referred to as "spa managers."

Figure 17:
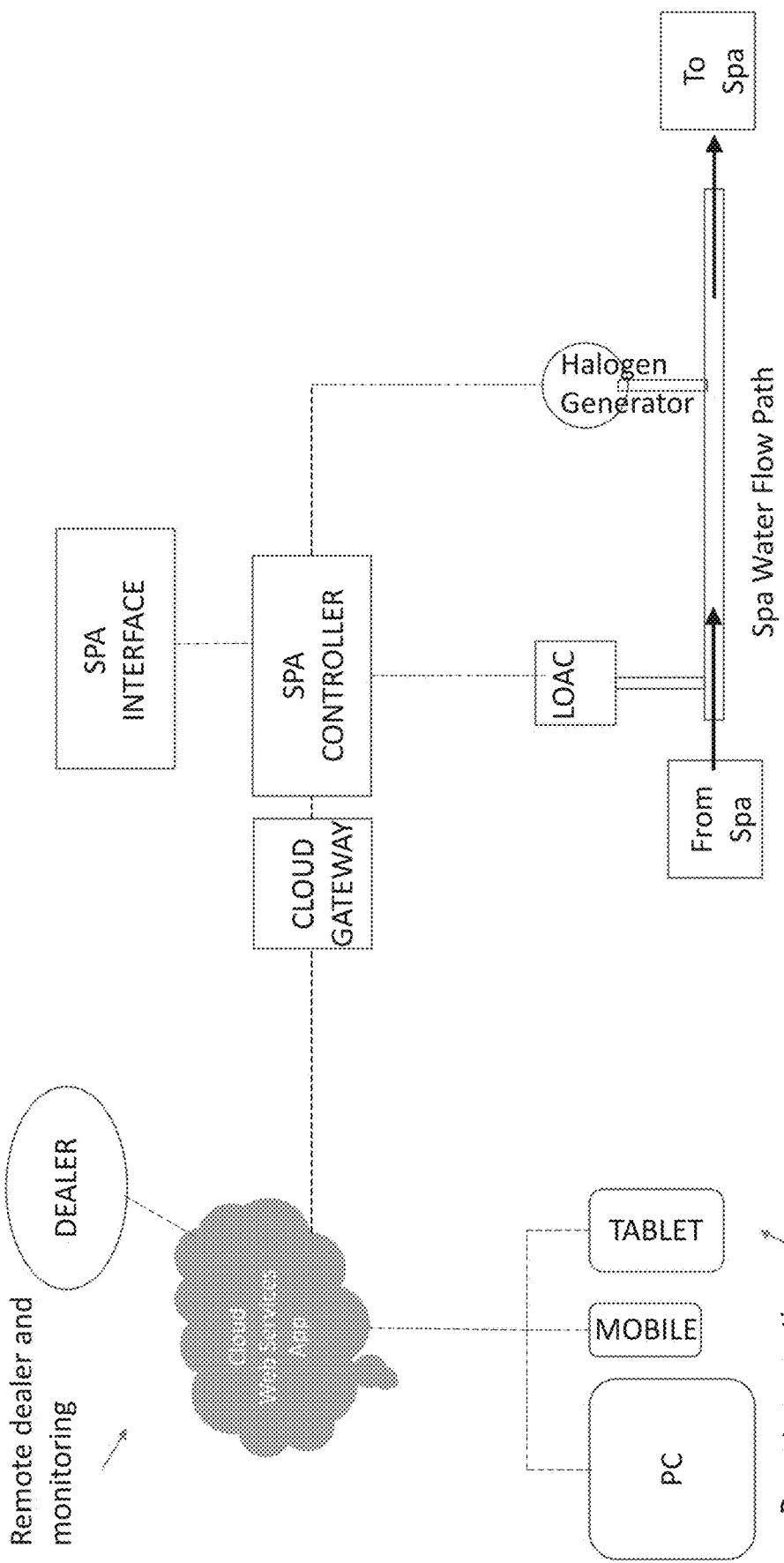
FIG. 17 depicts a block diagram of a second exemplary system including the LOAC sensor.

FIG. 17 depicts a second system of operating the LOAC sensor. This second system is the same as the first system in FIG. 16, with the exception that the second system is equipped with a halogen generator (e.g. chlorine or bromine). Based on the data provided by the LOAC sensor, the halogen generator is directed by the spa controller to generate and provide halogen in the spa as needed to maintain the proper levels in the spa water. The halogen generator can be coupled to a halogen doser as well. The sensor data allows the second system to determine when further halogen is needed.

Figure 18:
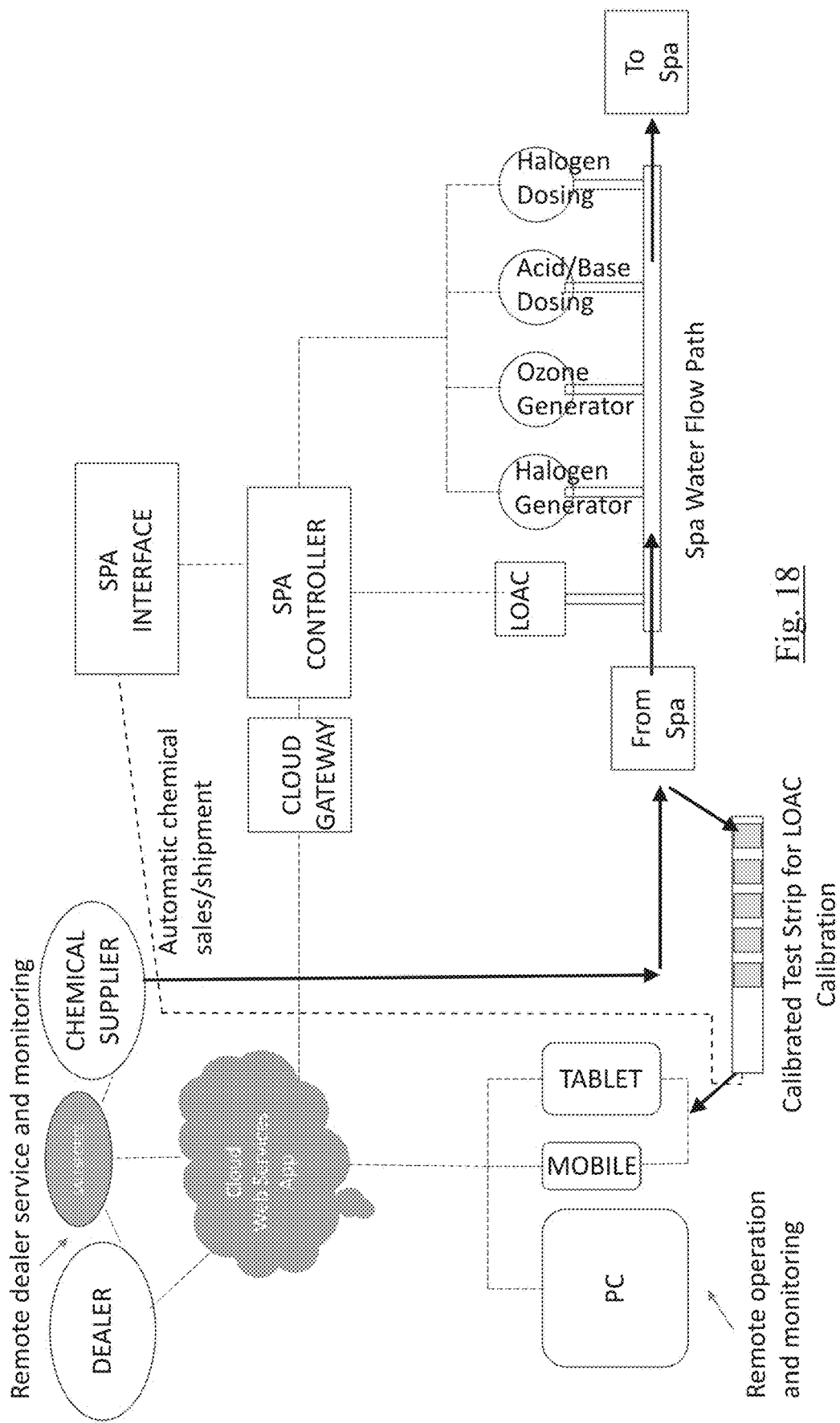
FIG. 18 depicts a block diagram of a third exemplary system including the LOAC sensor.

FIG. 18 depicts a third system of operating the LOAC sensor. This system is similar to those discussed in FIGS. 16-17, with the addition of several chemical treatment components. Chemical treatment components can include components to dose chemicals into the spa water and/or components to generate chemicals in the spa water. By way of example, such chemical treatment components include an ozone generator, an acid and/or base doser, and the halogen generator/dosing discussed with FIG. 17. Various additional chemical treatment components can also be installed. System feedback from the LOAC allows the spa controller to maintain the water with these added systems. As will be apparent, the more chemical treatment components installed in the system, the more automatic the system is. As shown by way of example in FIG. 18, the sensor assembly can be in fluid communication with one or more chemical treatment components that are also in fluid communication with the spa water. When the spa controller receives data from the sensor that the spa water requires additional chemicals, the spa controller can control the one or more chemical treatment components to input the chemicals into the spa water based on the data received and with minimal or no intervention by the spa managers.

As further shown in FIG. 18, the system can have automatic management/attention by third parties. Because the spa controller can be wirelessly connected to various processors to transmit, store, and display data, the spa controller can connect to a third party when the on-site components cannot adequately control the water quality. For example, the on-site chlorine generator or doser may be out of starting materials to adequately maintain the appropriate chlorine level. In this case, the spa controller can send data to a third party that has a sales force to sell a supply of the needed chlorine. Upon receiving this data, the sales force can sell and ship the chlorine to the spa user, and the spa controller can receive a signal that additional chlorine is in transit.

In another example, the spa controller can receive data that the spa water flow is abnormal, indicating a plugged filter. The spa controller can send this data to the spa dealer, indicating that maintenance is needed. Upon receiving this data, the dealer can schedule a maintenance appointment, and the spa controller can receive a signal that a maintenance appointment has been scheduled. When the spa water needs attention from a third party, the spa controller can send data indicating that the spa water needs attention to the third party by way of the one or more processors, and the spa controller can receive a signal from the one or more processors that the spa water will receive the attention needed. Any data received by the spa controller from a third party can be displayed to the spa user via the user interface. Additionally or alternatively, the spa user can use a smart phone, being wirelessly connected to the spa controller, to view any data transmitted, stored, or received by the spa controller.

The third system also includes optional field calibration by calibrated test strips. The spa user can insert a calibrated test strip into the spa for reading and/or recording a various water quality parameter (further media data). In this example, a mobile phone, smart phone, or other remote device can be used to take an image of the calibration readings, process it, and subsequently feed this collected data back to the spa controller via the cloud/internet. Alternatively or additionally, a spa manager can manually input the data received from the calibrated test strip into the system by way of the spa user interface. This reading could also be sent to third parties, such as the dealer or chemical supplier. The test strip data could be used to calibrate the LOAC sensor assembly and/or the various components of the sensor assembly and/or system.

In addition to FIGS. 16-18, the LOAC sensor assembly and operation system can have various other user interfaces for ease of operation. The LOAC sensor assembly can operate with side, on-board controls, it can have various lights to indicate various conditions of the water (e.g. green light for good quality), and the LOAC sensor assembly can be operated via various remote computer systems (e.g. laptop, desktop, smart phone applications, and the like). The LOAC sensor assembly can give various reminders and indicators of events to occur in the solution or media, such as timed events and maintenance reminders. The LOAC sensor assembly can be operational as part of a larger home system, such as a part of a home device hub for various parts of a home.

Several examples of managing this multi-functional water quality sensor are discussed below. All examples are based on a sensor as outlined in FIGS. 1 through 7. Examples 1 through 6 describe sensing modes. Examples 7-12 describe additional combination modes, and example 13 describes hypothetical configurations and modes.

Example 1

Apply a current of 0.5 mA to the temperature circuit, i.e. pad segments 12 and 15 of FIG. 1, with a variable temperature dependent resistance of approximately 600 Ohm, and documenting the voltage drop V over the resistor, pad segments 3 and 4 of FIG. 1, and feed the voltage into an algorithm:

$$dT_{(C)} = mV + b$$

where V is the voltage drop over resistor and m and b are empirically determined constants for slope and zero intercept. For purposes of this disclosure, "approximately" or "about" means within 10%, preferably within 5%, more preferably within 1% of a given quantity.

This example is producing a chip temperature as influenced by media it is exposed to. The sensor output is fast responding to temperature changes within time frame of milliseconds as illustrated by temperature decay pattern resulting from a heat pulse of 35 mW×0.2 sec imposed by heater circuit over pad segment 1 and 6 of FIG. 1. FIG. 8 shows the time resolved temperature profile following repeated heat pulses.

Example 2

Repeated application of heat pulses, as described in example 1, creates a chip temperature profile with peak and base temperatures. As an example—the peak temperature has successfully been inversely related to flow velocity via the algorithm:

$$F_{(T)} = a\left(1 + \left|\frac{\Delta T_{base}}{\Delta t}\right|\right)^l \cdot \left(1 + \frac{\Delta T_{cal}}{T_{cal}}\right)^m \cdot (\Delta T_{peak})^n + b$$

where a,b,l,m,n and $T_{cal}$ are material and sensor geometry dependent constants and $\Delta T/\Delta t$, $\Delta T_{cal}$, $\Delta T_{base}$ and $\Delta T_{peak}$ are variables derived from documentation of sensor temperature (T) over time (t). The algorithm has five elements:

(1) $n^{th}$ power element is the pulse height that correlates to flow, (2) the $m^{th}$ power element is a temperature calibration that corrects for change in pulse power with temperature, necessitated by convenience of using constant potential excitation rather than constant power excitation, (3) the $l^{th}$ power element corrects the peak height during base temperature changes, (4) the a element is a velocity—cross section area adjustment, and (5) the b element is a zero point adjustment.

This algorithm correlates the flow with the temperature increase as documented by sensor induced by a power load to the heater circuit located close to the sensor. The RTD sensor response to the change in flow is shown in FIG. 5. Sensors documenting flow through cooling rate are generally known as anemometers. As such, the inventive concept could be referred to as a pulse anemometer.

Examples 3-6

A spa bath chemistry was created using city water and additions of dichlorocyanuric acid, DCCy, to adjust chlorination level, additions of sodium bisulfate to decrease pH, sodium bicarbonate to increase pH and sodium chloride to increase conductivity without adjusting pH. A number of bath chemistries were created while documenting conductivity, ORP and pH with LOAC sensor and calibrated independent sensors. The flow velocity over the sensor during conductivity, ORP and pH documentation was in range of 1 m/sec.

Example 3

Application of AC potential to pad segments 7 and 8 of FIG. 1 produces a current response that is a variable of the conducting media separating the electrodes. FIG. 11 shows time resolved result of such a documentation using 6.2 kHz, +−0.25V square wave. Documentation of voltage drop over a known resistor produces a conductivity of the media in its simpler form via the algorithm for the conductivity of the media $\sigma_s$:

$$\sigma_s = a \cdot \frac{V_{re}}{R_{re}(V_{tot} - V_{re})} S$$

where a is material constant, $V_{re}$ is the voltage drop over the resistor $R_{re}$, and $V_{tot}$ the applied voltage amplitude. Elaboration on the algorithm can be done to take into account absolute temperature and resistance of the leads.

Example 4

Application of a DC potential signal over pad segments 9 and 11, $V_{WE-CE}$, induces a potential difference between pad segments 10 and 11, $V_{WE-RE}$. $V_{ORP}$ can be correlated to $V_{EW-ER}$ via the linear algorithm:

$$V_{ORP} = aV_{we-re} + b$$

where a and b are empirically determined constants. Using a=−1.314, b=1.7519, for example, a correlation between the LOAC independently determined ORP was created as depicted in FIG. 11. The ORP vs $V_{EW-ER}$ is geometry dependent—the example is created from geometry of FIG. 1 in galvanostatic controlled mode using 600 nA and document $V_{EW-ER}$ as average polarization in 10-12 seconds interval. Similar results are found in potentiostatic mode using $V_{WE-CE}$ polarizations between 0.8 V and 1.4 V.

Example 5

Application of two DC potential signals over pad segments 9 and 11, $V_{WE-CE}$, induces two potential differences between pad segments 10 and 11, $V_{WE-RE}$ pH can be correlated to $\Delta V_{WE-RE}$ via the linear algorithm:

$$pH = a\Delta V_{(we-re)_{21}} + b$$

where the two polarizations are indexed 2 and 1. The pH vs $\Delta V_{WE-RE}$ is geometry and chemistry dependent—the example is created from geometry of FIG. 1 in galvanostatic controlled mode using 600 nA and document $V_{we-re}$ as average polarization in 10-12 seconds interval. The chemistry was rich in chloride and the correlation is shown in FIG. 13. Similar results are found in potentiostatic mode using $V_{WE-CE}$ polarizations between 0.8 V and 1.4 V.

Example 6

Application of a two DC potential signals over pad segments 9 and 11, $V_{WE-CE}$, induces two potential differences between pad 10 and 11, $V_{WE-RE}$. pH can be correlated to $\Delta V_{WE-RE}$ via the linear algorithm:

$$pH = a\Delta V_{(we-re)_{21}} + b$$

where the two polarizations are indexed 2 and 1. The pH vs $\Delta V_{WE-RE}$ is geometry and chemistry dependent—the example is created from geometry of FIG. 1 in galvanostatic controlled mode using 600 nA and document $V_{EW-ER}$ as average polarization in 10-12 seconds interval. The water was in this series of experiments chloride arm i.e. sodium chloride not added to spa chemistry.

Changing the water chemistry to be chloride low changes the pH dependence. Following correlation was found as shown in FIG. 14. Similar results are found in potentiostatic mode using $V_{WE-CE}$ polarizations between 0.8V and 1.4V.

Examples 7-10

Combination of sensing modes in several cases increase the information value of the individual sensing modes.

Example 7

Examples 1 and 2 described temperature and flow documentation individually by the LOAC. However the pulse approach of Example 2 allows us simultaneously to document temperature and flow. Base temperatures are separating the pulse induced peak temperatures. The base temperatures are directly related to the media temperature given appropriate spacing of pulses. In the example, the flow rate can be resolved to sub-second basis. One of the inventive features is the use of this pulsed power which allows the use of the LOAC RTD to document both flow and temperature without need for additional RTD circuitry to document a reference temperature against which peak temperature otherwise would have to be documented.

Example 8

Examples 4, 5 and 6 show one or more polarizations as the basis for ORP and pH documentation. One would adopt one of the polarizations used for documenting ORP as one of two polarizations used for pH documentation.

Example 9

There are two special cases for evaluation of pH response of the LOAC. Combining the conductivity measure with the choice of pH algorithm allows, for example, to base the most appropriate algorithm on conductivity and, if available, set-up and maintenance history.

Example 10

Total dissolved salt, TDS, can be extrapolated from conductivity measures, see Example 3. In this example, First, conductivity corrected for temperature is determined.

$$\sigma_{s(T)} = \sigma_{s(T=20)}(1 + 0.02\Delta T)$$

Then corrected for specific ionic conductivity assuming the conductivity is based on i.e. sodium chloride:

$$TDS = 2.2 \cdot \sigma_{s(T)}$$

Examples 11-12

Interference between measurement modes can be a practical issue overcome conveniently by adopting management practices.

Example 11

Conductivity, pH and ORP electrodes are in combination representing sources of cross over noise making it cumbersome to document conductivity and ORP and conductivity and pH simultaneously. Conductivity, pH and ORP in general are used as basis for maintenance decisions and rapid changes in conductivity, pH and ORP are rare beyond immediately following chemistry maintenance events. Separating in time on one side conductivity and on the other side pH and ORP documentation does therefore not represent a reduction in information retrieved from the LOAC sensor.

Example 12

Example 4, 5 and 6 provided conductivity, ORP and pH information using electrodes 17,18,19,20 and 21. As an example we could use any two electrode combination: 17-18, 17-19, 17-20 . . . but more interesting 19-21 to document conductivity and if adopted eliminating need for electrode 17-18. The bottom line is that in principal, any 2 electrode combination can be used for conductivity documentation and any 3 electrode combination can be used for ORP and pH documentation. We have found that a preferred three electrode combination represented by 19,20 and 21 is optimal for pH ORP in which case electrodes 19 and 21 would be used for conductivity. We have found that a preferred five electrode combination represented by 19, 20 and 21 for pH ORP and 17-18 for conductivity are optimal.

Hypothetical Example 13

Several additional features can be imagined for the three electrode combination represented by electrode 19, 20 and 21 of FIG. 1.

Example 13

Focusing on the reference electrode RE. The reference electrode is of platinum creating general unbiased sensitivity to redox pairs present in solution. Changing electrode material or surface coating to ligand types or covering the electrode with an ion or dissolved gas selective membrane represent an avenue to tailor LOAC sensor to specific sensitivity. For example bonding proteins like immunoglobuline or EDTA will create specific sensitivity to antibodies or calcium respectively while coverage of reference electrode with Nafion or PVC will create selectivity for protons and oxygen/chlorine/ozone respectively. The sensitized reference electrode will create unique polarization relative to Vwe-ce polarization similarly as described for ORP and pH relations in examples 4, 5 and 6.

The above examples give a picture of the scope of the invention but should not be considered limiting for the applications possible.

The subject disclosure provides a multi-functional sensor that determines both temperature and flow using the same sensor circuit by using a heat pulse technique. The sensor also determines pH, ORP and chlorine levels using a single dedicated three electrode sensor operated in a dynamic mode. Additionally, sequential sensing operation is provided to reduce sensing interference during the various sensing operations.

Thus, a multi-functional sensor is provided for optional sensing of temperature, flow, conductivity, ORP, pH, alkalinity, cyanuric acid concentration, and/or oxidant concentration that is comprised of an electrically non-conductive substrate covered with electrically conductive traces patterned out over three regions defined as a proximal region, intermediary region, and distal region. The proximal region is exposed to the media to be sensed and holds at least three conductive traces serving as electrodes for optional conductivity, ORP and pH sensing. The intermediary region is insulated from the media to be sensed and holds at least two conductive traces serving as electrical circuits for optional temperature and flow sensing of the media. The distal region is also insulated from the media and holds conductive traces connected to the proximal electrode traces and intermediary circuit traces. The traces on the distal region terminate in pads that serve as an interface for external connection to sensor.

As discussed above, the three conductive traces that serve as electrodes optionally comprise three concentric circles that are interrupted on their circumferences to connect to the traces. The radially outer electrode is the counter electrode, the radially inner electrode is the working electrode, and the radially intermediary electrode between the inner and outer electrodes is the reference electrode. The electrodes may also be linear.

A pulse anemometer mode of operating the multi-functional sensor includes the following steps. A temperature profile is created that is comprised of peak and valley temperatures of the substrate exposed to a media via heat pulses defined by a power, a power duration, and a power off duration. The peak and valley temperatures of the substrate are documented as a measure of the flow and velocity of the media. In one example, the power duration is between 0.01 seconds and 0.5 seconds, and the power off duration is at least 0.3 seconds.

A dynamic mode of operating a three electrode setup for ORP documentation includes the following steps. A constant potential or a constant current is established between the working electrode and the counter electrode. The potential between the working electrode and the reference electrode is documented as a measure of the ORP. In one example, the constant potential between the working electrode and counter electrode should be chosen between 0.8 V and 2.0 V, or between −0.8V and −2.0V. In one example, the first constant current between working electrode and counter electrode should be chosen between 100 and 600 nA, or between −100 and −600 nA.

A dynamic mode of operating a three electrode setup for pH and/or alkalinity documentation includes the following steps. A first constant potential or a first constant current is established between the working electrode and the counter electrode. The potential between the working electrode and the reference electrode is defined as a first documented potential. A second constant potential or a second constant current is established between the working electrode and the counter electrode. The potential between the working electrode and the reference electrode for this is then defined as a second documented potential. The difference between the first and second documented potentials between the working and reference electrodes is established as a measure of the pH. The alkalinity of the media is determined from the pH. In one example, the first constant potential between the working electrode and counter electrode should be chosen between 0.8 V and 2.0 V, or between −0.8 V and −2.0 V. In one example, the second constant potential between the working electrode and counter electrode should be chosen between 0.8 V and 2.0 V, or between −0.8 V and −2.0 V such that the difference between the two potentials is at least 0.2 V but does not exceed 0.6 V. In one example, the first constant current between the working electrode and counter electrode should be chosen between 100 and 600 nA, or between −100 and −600 nA. In one example, the second constant current between the working electrode and counter electrode should be chosen between 100 and 600 nA, or between −100 and −600 nA, such that the difference between the two currents is at least 100 nA but does not exceed 400 nA.

Further examples of materials or processing of the multi-functional sensor include the following. In one example, the conductive trace that forms the reference electrode is optionally covered by an ion selective membrane, a gas permeable membrane, or a carbon coating. In one example, the ion selective coating is nafion. In one example, the gas permeable coating is PVC. In one example, the carbon coating is a DLC or a ta:C coating optionally modified with ligands. In one example, the ligands can comprise ethylenediamminenetetraacetate (EDTA).

The subject sensor assembly, in one example, comprises a silicon chip with electrodes, circuitries, leads and pads made of platinum mounted on and wire bonded to a printed circuit board as described above. The sensor assembly is inserted in a housing and potted with a resin such that the chip electrodes are exposed to the exterior while the circuitries, leads, pads are insulated from the exterior by resin and the housing. In one example, the housing is equipped with features for bayonet fitting to a T connection and the PCB is equipped with a jack for external connection (FIGS. 6-7). In one example, the housing is molded in glass filled polypropylene and the silicon material for the chip substrate is a nonconductive grade having a thickness 0.55 mm or less. In one example, the silicon chip with the circuitries has been annealed at 375 degrees C. for two hours in an inert atmosphere. In one example, the platinum material has been deposited in a sputtering process starting with titanium in a thickness of 100 nm range overcoated with platinum in a 1000 nm thickness range.

Optionally, the circuitries and leads are overcoated with a coating chosen from materials such as, PtO, SiNx, SiNxOy, SiNixOyCz, for example, in a thickness of more than about 1000 nm.

The individual sensing function and any combination of the multiple principal sensor functions and derivatives of these functions such as equivalent chlorine sensing, equivalent ozone sensing, equivalent Total Dissolved Salt, TDS can also be determined with the subject sensor. Further, a sensor noise reduction is provided by the use of a grounded inlet-outlet grid in a T-connection. The T-connection thus includes a noise reduction feature in the form of grounded metal mesh material, for example, that "filters" the flow of some corrosion resistant materials, such as NiSn cladded copper, for example. The mesh has a mesh size providing minimal pressure drop, such as 0.2 mm wire gauge woven in mesh size of 1 mm×1 mm for example, and connected to ground. In one example, there are meshes at the entrance and exit of the T-connection housing the sensing volume.

One purpose of this disclosure is to provide an inexpensive unified sensor package with ability to output measures of temperature, flow, conductivity, ORP, pH, alkalinity, cyanuric acid concentration, and/or oxidant concentration in continuous operation with an accuracy sufficient to provide feedback for safe spa operation. While one aim for the disclosed subject matter—is use in a spa bath the size, design, cost and concepts making up the disclosure lend itself equally well to a broad range of applications calling for individual or combined in situ documentation of temperature, flow, conductivity, ORP, pH, alkalinity, cyanuric acid concentration, and/or oxidant concentration and the derivatives thereof such as equivalent chlorine, oxygen or ozone concentration as well as Total Dissolved Salt (TDS). Further, specifics of the configuration lend itself well to continued development accomplished by mode of operation sophistication as well as electrode modifications.

The subject disclosure can be used for water quality determinations in a spa application as well as in pool water, in city water quality characterization for commercial and domestic use, washing machines, dish washers, coffee brewers, soft drink dispensers, drinking fountains, faucets, thermostats for faucets, ice makers, water dispensers, fridge water dispensers, conditioned water dispensers such as chlorinated water dispensers, ozonated water dispensers, sterilized water dispensers, in filter applications, reverse osmosis filter applications, in electrolyzer applications, and in fuel cell applications, for example. It also be used in medical applications such as in situ flow and blood characterization applications, in renal and urine characterization applications. The claimed sensor platform approach lends itself well to customization in mass production at a low price point due to common chip design for manufacture of sensors for an array of application.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The invention claimed is:

1. A multi-functional water quality sensor assembly comprising an electrically non-conductive substrate defining at least a distal region, intermediary region, and proximal region that are each covered with electrically conductive traces, and wherein the proximal region is configured to be exposed to water to be sensed and wherein the distal and intermediary regions are configured to be protected from the water, and wherein the electrically conductive traces connect to one or more proximal electrodes to sense one or more of alkalinity, cyanuric acid concentration, or oxidant concentration of the water, wherein the proximal region includes the one or more proximal electrodes, the intermediary region includes electrical circuits to sense temperature and flow of the water, and the distal region includes electrically conductive trace segments that terminate in pads serving as an external electrical connection interface.

2. The multi-functional water quality sensor assembly according to claim 1, wherein the one or more proximal electrodes comprise at least three proximal electrodes configured to sense one or more of conductivity, oxidation reduction potential (ORP), or acidity (pH) of the water.

3. The multi-functional water quality sensor assembly according to claim 2, wherein the at least three electrodes are each linear and arranged side-by-side in a row and include a first conductivity electrode, a second conductivity electrode, a counter electrode, and a reference electrode that are operable to sense the conductivity of the water, wherein the counter and reference electrodes are positioned between the conductivity electrodes.

4. The multi-functional water quality sensor assembly according to claim 3, wherein the conductivity sensed via the first conductivity electrode, the second conductivity electrode, the counter electrode, and the reference electrode is used to determine cyanuric acid concentration of the water.

5. The multi-functional water quality sensor assembly according to claim 2, wherein the at least three electrodes are each linear and arranged side-by-side in a row and include a counter electrode, a reference electrode, and a working electrode that are operable to sense the pH of the water, wherein the reference electrode is positioned between the counter and working electrodes.

6. The multi-functional water quality sensor assembly according to claim 5, wherein the sensed pH is used to determine cyanuric acid concentration of the water.

7. The multi-functional water quality sensor assembly according to claim 1, wherein the electrodes are configured to sense conductivity and one or both of oxidation reduction potential (ORP) or acidity (pH) and include five electrodes that are each linear, the five electrodes arranged side-by-side in a row so that a first electrode is a first conductivity electrode, a second electrode is a counter electrode, a third electrode is a reference electrode, a fourth electrode is a working electrode, and a fifth electrode is a second conductivity electrode.

8. The multi-functional water quality sensor assembly according to claim 1, further comprising a spa controller and one or more chemical treatment components, the spa controller operable to receive data from the electrically conductive traces and the one or more electrodes, and the spa controller operable to control the one or more chemical treatment components to input chemicals into the water based on the data received.

9. The multi-functional water quality sensor assembly according to claim 8, wherein the spa controller is wirelessly connected to one or more processors that transmits, stores, and displays the data to one or more spa managers.

10. An apparatus, comprising:
a housing including a body having an end and an opening; and
the sensor assembly according to claim 1, wherein the proximal region extends through the opening and axially beyond the end of the body of the housing, and wherein the housing is sealed to establish a barrier against media ingress to the distal and intermediary regions.

11. The apparatus of claim 10, wherein the housing is potted and sealed with resin to establish a barrier against ingress of the water to the distal and intermediary regions such that only the proximal region is configured to be exposed to the water.

12. The apparatus of claim 11, wherein the intermediary region holds the heater and RTD circuits that are entirely overpotted inside the housing, the distal region holds leads to the heater and RTD circuits and pads for external connectivity, and the proximal region carries at least one of a pH electrode, an ORP electrode, or a conductivity electrode.

13. The apparatus of claim 10, wherein the housing is configured to be coupled to a conduit defining a flow path for the water such that when the housing is coupled to the conduit, the proximal region extends into and intersects the flow path.

14. The multi-functional water quality sensor assembly of claim 1, wherein the substrate is composed of glass and the electrically conductive traces include titanium overcoated with platinum.

15. The multi-functional water quality sensor assembly of claim 1, wherein the substrate is comprised of a chip.

16. The multi-functional water quality sensor assembly of claim 15, wherein the chip is less than or equal to 4.0 mm by 1.0 mm by 0.5 mm.

17. The multi-functional water quality sensor assembly of claim 1, wherein the flow is derived from a temperature sensor when a heater circuit is powered.

18. A multi-functional water quality sensor assembly comprising:
an electrically non-conductive substrate defining at least a distal region, intermediary region, and proximal region that are each covered with electrically conductive traces;
a printed circuit board connected to the distal region; and
a housing enclosing the intermediary and distal regions, and surrounding at least one end of the printed circuit board, and wherein the proximal region extends outwardly of the housing to be exposed to water to be sensed, and
wherein the electrically conductive traces comprise at least electrical circuits to sense temperature and flow of the water and one or more electrodes to sense one or more of alkalinity, cyanuric acid concentration, or oxidant concentration of the water, wherein the electrical circuits comprise a heater circuit including a resistive heating element located in the intermediary region and heater circuit segments located in the distal region, and a resistive temperature detector circuit including a resistive temperature detector located in the intermediary region and resistive temperature detector segments located in the distal region and that is used to determine temperature and flow rate of the water.

19. The multi-functional water quality sensor assembly according to claim 18, wherein the one or more electrodes includes a plurality of electrodes that are each linear and arranged side-by-side in a row and that include a first conductivity electrode, a second conductivity electrode, a counter electrode, and a reference electrode that are operable to sense the conductivity of the water, wherein the counter and reference electrodes are positioned between the conductivity electrodes.

20. The multi-functional water quality sensor assembly according to claim 19, wherein the conductivity sensed via the first conductivity electrode, the second conductivity electrode, the counter electrode, and the reference electrode is used to determine one or more of the cyanuric acid concentration or the oxidant concentration of the water.

21. The multi-functional water quality sensor assembly according to claim 18, wherein the one or more electrodes includes a plurality of electrodes that are each linear and arranged side-by-side in a row and that include a counter electrode, a reference electrode, and a working electrode that are operable to sense the pH of the water, and the pH measurement determines one or more of the alkalinity, the oxidant concentration, or the cyanuric acid concentration of the water, and wherein the reference electrode is positioned between the counter and working electrodes.

22. The multi-functional water quality sensor assembly according to claim 18, wherein the one or more electrodes includes five electrodes that are each linear, the five electrodes arranged side-by-side in a row so that a first electrode is a first conductivity electrode, a second electrode is a counter electrode, a third electrode is a reference electrode, a fourth electrode is a working electrode, and a fifth electrode is a second conductivity electrode.

* * * * *